(12) United States Patent
Kawana et al.

(10) Patent No.: US 10,179,780 B2
(45) Date of Patent: Jan. 15, 2019

(54) AZOLE BENZENE DERIVATIVE AND CRYSTALLINE FORM THEREOF

(71) Applicant: TEIJIN PHARMA LIMITED, Tokyo (JP)

(72) Inventors: Asahi Kawana, Tokyo (JP); Hisae Nozato, Tokyo (JP); Chikashi Kanazawa, Tokyo (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 15/329,813

(22) PCT Filed: Jul. 29, 2015

(86) PCT No.: PCT/JP2015/071530
§ 371 (c)(1),
(2) Date: Jan. 27, 2017

(87) PCT Pub. No.: WO2016/017708
PCT Pub. Date: Feb. 4, 2016

(65) Prior Publication Data
US 2017/0247364 A1    Aug. 31, 2017

(30) Foreign Application Priority Data

Jul. 30, 2014 (JP) ................... 2014-155030
Jul. 30, 2014 (JP) ................... 2014-155032

(51) Int. Cl.
*C07D 417/10* (2006.01)
*A61K 31/427* (2006.01)

(52) U.S. Cl.
CPC .......... *C07D 417/10* (2013.01); *A61K 31/427* (2013.01); *C07B 2200/13* (2013.01)

(58) Field of Classification Search
None
See application file for complete search history.

(56) References Cited

U.S. PATENT DOCUMENTS

| 5,843,969 A | 12/1998 | Ota et al. |
| 2009/0306396 A1 | 12/2009 | Toyoshima et al. |
| 2010/0227864 A1 | 9/2010 | Shimizu et al. |
| 2015/0376174 A1* | 12/2015 | Kawana ............... C07D 417/10 514/365 |

FOREIGN PATENT DOCUMENTS

| EP | 0513379 A1 | 11/1992 |
| EP | 1020454 A1 | 7/2000 |
| WO | 96/31211 A1 | 10/1996 |
| WO | 2007/043400 A1 | 4/2007 |
| WO | 2008/126770 A1 | 10/2008 |
| WO | 2008/126899 A1 | 10/2008 |
| WO | 2011/101867 A2 | 8/2011 |
| WO | 2014/119681 A1 | 8/2014 |

OTHER PUBLICATIONS

Byrn et al., Pharmaceutical Research; vol. 12, No. 7, pp. 945-954 (1996).*
Berge et al. J. Pharm. Sci., 1977, 66 (1), 1-19.*
International Search Report of PCT/JP2015/071530, dated Sep. 15, 2015. [PCT/ISA/210].
Communication dated May 19, 2017 issued by the European Patent Office in counterpart application No. 15827218.7.

* cited by examiner

*Primary Examiner* — Alicia L Otton
(74) *Attorney, Agent, or Firm* — Sughrue Mion, PLLC

(57) ABSTRACT

There are provided: 4-methyl-2-[4-(2-methylpropoxy)-3-(1H-1,2,3,4-tetrazol-1-yl)phenyl]-1,3-thiazole-5-carboxylic acid, a sodium salt thereof and crystals of these, useful as a therapeutic agent and a prophylactic agent for gout, hyperuricemia and the like, and a method for producing the same.

39 Claims, 10 Drawing Sheets

AZOLE BENZENE DERIVATIVE AND CRYSTALLINE FORM THEREOF

CROSS REFERENCE TO RELATED APPLICATIONS

This application is a National Stage of International Application No. PCT/JP2015/071530 filed Jul. 29, 2015, claiming priority based on Japanese Patent Application Nos. 2014-155030, filed Jul. 30, 2014, and 2014-155032, filed Jul. 30, 2014.

TECHNICAL FIELD

The present invention relates to a novel azole benzene derivative and a crystal thereof useful as a therapeutic agent or a prophylactic agent for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary diseases, inflammatory bowel diseases or autoimmune diseases, and a production method of the crystal.

BACKGROUND ART

Xanthine oxidase is an enzyme catalyzing the conversion of hypoxanthine to xanthine and further to uric acid in nucleic acid metabolism.

A xanthine oxidase inhibitor inhibits uric acid synthesis to reduce a level of uric acid in the blood with respect to the action of xanthine oxidase. That is, a xanthine oxidase inhibitor is effective as a therapeutic agent for hyperuricemia and various diseases caused by hyperuricemia. On the other hand, there are gouty arthritis and gouty tophus called gout as a clinical condition caused by a result of deposition of urate crystals after prolonged hyperuricemia. In addition, hyperuricemia is considered to be important as a factor of lifestyle diseases associated with obesity, hypertension, dyslipidemia and diabetes or metabolic syndromes, and recently, it has been clarified that hyperuricemia is a risk factor of renal damage, urinary calculi and cardiovascular diseases by epidemiological surveys (The Guideline Revising Committee of Japanese Society of Gout and Nucleic Acid Metabolism, ed., Guideline for the management of hyperuricemia and gout, second edition, Medical Review (2010)). In addition, a xanthine oxidase inhibitor is expected to be useful for the treatment of diseases associated with active oxygen species by inhibitory activity against the active oxygen species generation, for example, for the treatment of cardiovascular diseases through the vascular function-improving action (Circulation. 2006; 114: 2508-2516).

Allopurinol and febuxostat are clinically used as a therapeutic agent for hyperuricemia, but allopurinol has been reported to have a side effect such as Stevens-Johnson syndrome, toxic epidermal necrolysis, hepatic disorder and renal dysfunction (Nippon Rinsho, 2003; 61, Suppl. 1: 197-201).

As a compound having a xanthine oxidase inhibitory activity, for example, a 2-phenylthiazole derivative is reported (PTL 1 to 3).

On the other hand, in PTL 4 and 5, a dithiazole carboxylic acid derivative having a benzene ring in the center is reported. Further, in PTL 6 and 7, a biphenyl thiazole carboxylic acid derivative is reported.

CITATION LIST

Patent Literature

[PTL 1] international Publication No. 92/09279
[PTL 2] Japanese Patent Laid-Open No. 2002-105067
[PTL 3] international Publication No. 96/31211
[PTL 4] international Publication No. 2011/139886
[PTL 5] international Publication No. 2011/101867
[PTL 6] international Publication No. 2010/018458
[PTL 7] International Publication No. 2010/128163

SUMMARY OF INVENTION

Technical Problem

An object of the present invention is to provide a novel compound and a crystal thereof useful as a therapeutic agent or a prophylactic agent for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary diseases, inflammatory bowel diseases or autoimmune diseases. In addition, another object is to provide a method of reproducibly producing the crystal which is chemically stable and suitable for an active pharmaceutical ingredient.

Solution to Problem

As a result of earnest studies with the above objects, the present inventors have found that 4-methyl-2-[4-(2-methylpropoxy)-3-(1H-1,2,3,4-tetrazol-1-yl)phenyl]-1,3-thiazole-5-carboxylic acid (hereinafter, also referred to as compound (I)) has an excellent uric acid lowering effect as a xanthine oxidase inhibitor, is capable of crystallization and exists as at least three types of crystal polymorphs. In addition, the present inventors have found that the crystal polymorphs can be selectively produced. Further, the present inventors have found that sodium 4-methyl-2-[4-(2-methylpropoxy)-3-(1H-1,2,3,4-tetrazol-1-yl)phenyl]-1,3-thiazole-5-carboxylate (hereinafter, also referred to as compound (II)) has an excellent uric acid lowering effect as a xanthine oxidase inhibitor and that the compound (II) can be crystallized.

That is, the present invention provides the following.
[1] A crystal of 4-methyl-2-[4-(2-methylpropoxy)-3-(1H-1,2,3,4-tetrazol-1-yl)phenyl]-1,3-thiazole-5-carboxylic acid;
[2] The crystal according to [1], wherein the crystal has a crystal form A;
[3] The crystal according to [2], wherein the crystal has characteristic peaks at diffraction angles of 2θ=8.6°, 10.2°, 13.3°, 14.4°, 18.5°, 19.9°, 21.8°, 25.1°, 25.6°, 26.6°, 27.1° and 29.5° in its powder X-ray diffraction spectrum;
[4] The crystal according to [2], wherein its powder ray diffraction spectrum has a pattern shown in FIG. 1;
[5] The crystal according to [2], wherein the crystal has characteristic peaks at chemical shifts of 116.3 ppm, 117.6 ppm, 120.0 ppm, 123.6 ppm, 125.9 ppm, 127.4 ppm, 143.7 ppm, 151.8 ppm, 161.1 ppm, 162.3 ppm and 165.5 ppm in its solid-state $^{13}$C NMR spectrum;

[6] The crystal according to [2], wherein its solid-state $^{13}$C NMR spectrum has a pattern shown in FIG. 5;

[7] The crystal according to [2], wherein the crystal has characteristic peaks at wave numbers of 745 cm$^{-1}$, 822 cm$^{-1}$, 889 cm$^{-1}$, 975 cm$^{-1}$, 997 cm$^{-1}$, 1611 cm$^{-1}$ and 1705 cm$^{-1}$ in its infrared absorption spectrum (KBr method);

[8] The crystal according to [2], wherein its infrared absorption spectrum (KBr method) has a pattern shown in FIG. 8;

[9] The crystal according to [2], wherein its exothermic peak in thermogravimetry/differential thermal analysis is at 222° C.;

[10] The crystal according to [1], wherein the crystal has a crystal form B;

[11] The crystal according to [10], wherein the crystal has characteristic peaks at diffraction angles of 2θ=10.1°, 12.6°, 13.1°, 14.0°, 18.6°, 24.2°, 25.2°, 25.7°, 27.2° and 30.5° in its powder X-ray diffraction spectrum;

[12] The crystal according to [10], wherein its powder X-ray diffraction spectrum has a pattern shown in FIG. 2;

[13] The crystal according to [10], wherein the crystal has characteristic peaks at chemical shifts of 115.4 ppm, 118.0 ppm, 119.8 ppm, 123.2 ppm, 126.4 ppm, 129.1 ppm, 142.7 ppm, 151.2 ppm, 160.9 ppm and 166.6 ppm in its solid-state $^{13}$C NMR spectrum;

[14] The crystal according to [10], wherein its solid-state $^{13}$C NMR spectrum has a pattern shown in FIG. 6;

[15] The crystal according to [10], wherein the crystal has characteristic peaks at wave numbers of 744 cm$^{-1}$, 810 cm$^{-1}$, 972 cm$^{-}$, 997 cm$^{-1}$, 1005 cm$^{-1}$, 1611 cm$^{-1}$ and 1710 cm$^{-1}$ in its infrared absorption spectrum (KBr method);

[16] The crystal according to [10], wherein its infrared absorption spectrum (KBr method) has a pattern shown in FIG. 9;

[17] The crystal according to [10], wherein its exothermic peak in thermogravimetry/differential thermal analysis is at 225° C. and it is an anhydrous crystal;

[18] The crystal according to [1], wherein the crystal has a crystal form C;

[19] The crystal according to [18], wherein the crystal has characteristic peaks at diffraction angles of 2θ=7.2°, 12.5°, 13.0°, 14.7°, 19.2°, 20.0°, 21.4°, 21.7°, 24.7° and 26.0° in its powder X-ray diffraction spectrum;

[20] The crystal according to [18], wherein its powder X-ray diffraction spectrum has a pattern shown in FIG. 3;

[21] The crystal according to [18], wherein the crystal has characteristic peaks at chemical shifts of 116.1 ppm, 119.6 ppm, 123.1 ppm, 126.1 ppm, 127.1 ppm, 130.0 ppm, 143.6 ppm, 150.3 ppm, 158.3 ppm, 160.7 ppm, 163.9 ppm, 165.5 ppm and 167.0 ppm in its solid-state $^{13}$C NMR spectrum;

[22] The crystal according to [18], wherein its solid-state $^{13}$C NMR spectrum has a pattern shown in FIG. 7;

[23] The crystal according to [18], wherein the crystal has characteristic peaks at wave numbers of 745 cm$^{-1}$, 751 cm$^{-1}$, 809 cm$^{-1}$, 820 cm$^{-1}$, 971 cm$^{-1}$, 1006 cm$^{-1}$, 1613 cm$^{-1}$, 1682 cm$^{-1}$ and 1710 cm$^{-1}$ in its infrared absorption spectrum (KBr method);

[24] The crystal according to [18], wherein its infrared absorption spectrum (KBr method) has a pattern shown in FIG. 10;

[25] The crystal according to [18], wherein its endothermic peak is at 88° C. and exothermic peak is at 225° C. in thermogravimetry/differential thermal analysis;

[26] Sodium 4-methyl-2-[4-(2-methylpropoxy)-3-(1H-1,2,3,4-tetrazol-1-yl)phenyl]-1,3-thiazole-5-carboxylate;

[27] A crystal of the compound according to [26];

[28] The crystal according to [27], wherein the crystal has characteristic peaks at diffraction angles of 2θ=7.2°, 10.9°, 13.3°, 15.9°, 18.2°, 20.8°, 22.1°, 25.2°, 26.1° and 29.1° in its powder X-ray diffraction spectrum;

[29] The crystal according to [27], wherein its powder X-ray diffraction spectrum has a pattern shown in FIG. 4;

[30] The crystal according to [27], wherein its exothermic peak in thermogravimetry/differential thermal analysis is at 281° C.;

[31] A pharmaceutical composition comprising the compound or the crystal thereof according to any one of [1] to [30] and a pharmaceutically acceptable carrier;

[32] A xanthine oxidase inhibitor comprising the compound or the crystal thereof according to any one of [1] to [30] as an active ingredient;

[33] A therapeutic or prophylactic agent for one or more diseases selected from the group consisting of gout, hyperuricemia, tumor lysis syndrome, urinary calculi, hypertension, dyslipidemia, diabetes, cardiovascular diseases, kidney diseases, respiratory diseases, inflammatory bowel diseases and autoimmune diseases, comprising the compound or the crystal thereof according to any one of [1] to [30] as an active ingredient;

[34] A method for producing the crystal form A of 4-methyl-2-[4-(2-methylpropoxy)-3-(1H-1,2,3,4-tetrazol-1-yl)phenyl]-1,3-thiazole-5-carboxylic acid, comprising the steps of:

suspending an alkyl ester of 4-methyl-2-[4-(2-methylpropoxy)-3-(1H-1,2,3,4-tetrazol-1-yl)phenyl]-1,3-thiazole-5-carboxylic acid in a solvent and performing hydrolysis by adding an aqueous solution of a base thereto and neutralizing the reaction product;

[35] The method of production according to [34], further comprising the step of adding water to the neutralized product and stirring it;

[36] A method for producing the crystal form B of 4-methyl-2-[4-(2-methylpropoxy)-3-(1H-1,2,3,4-tetrazol-1-yl)phenyl]-1,3-thiazole-5-carboxylic acid, comprising the step of suspending the crystal form A of 4-methyl-2-[4-(2-methylpropoxy)-3-(1H-1,2,3,4-tetrazol-1-yl)phenyl]-1,3-thiazole-5-carboxylic acid in a solvent;

[37] The method of production according to [36], further comprising the step of heating the suspension;

[38] The method for producing the crystal according to [36] or [37], wherein the solvent is selected from the group consisting of ethers, ketones, esters, alcohols, water, and a mixture solvent thereof; and

[39] A method for producing the crystal form C of 4-methyl-2-[4-(2-methylpropoxy)-3-(1H-1,2,3,4-tetrazol-1-yl)phenyl]-1,3-thiazole-5-carboxylic acid, comprising crystallization from a N,N-dimethylformamide solution thereof.

Advantageous Effects of Invention

The present invention provides crystals of an azole benzene derivative, which are useful as therapeutic or prophylactic agents for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary diseases, inflammatory bowel diseases or autoimmune diseases, and the production method thereof. The crystal of the compound (I), or the compound (II) or the crystal thereof can be used as an active pharmaceutical ingredient for producing a pharmaceutical agent. In addition, the methods of the present invention for producing the crystal of the compound (I), or the compound (II) or the crystal thereof are suitable for industrial production.

DESCRIPTION OF EMBODIMENTS

Figure 1:
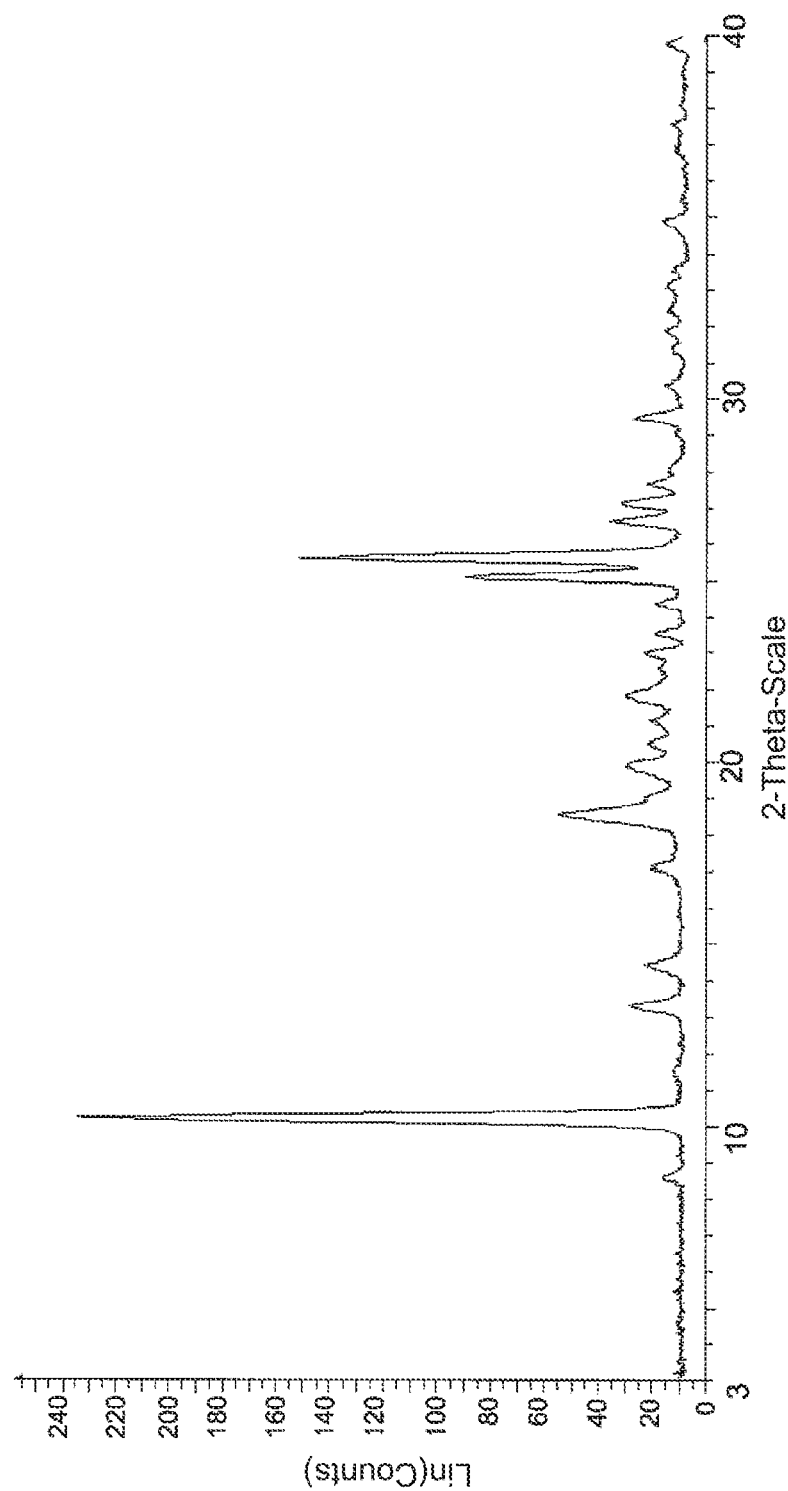
FIG. 1 is a powder X-ray diffraction spectrum of crystal form A of the compound (I).

"Xanthine oxidase" is used both in a broad sense that it is an enzyme for catalyzing an oxidation reaction from hypoxanthine to xanthine and further to uric acid and in a narrow sense that it is an oxidase type xanthine oxidoreductase which is one of the enzymes that catalyze the same reaction. In the present invention, unless otherwise specified, "xanthine oxidase" is collectively called an enzyme which catalyzes an oxidation reaction from hypoxanthine to xanthine and further to uric acid. Among the xanthine oxidoreductase which is responsible for this reaction, two types of oxidase type oxidoreductase and dehydrogenase type oxidoreductase are present and both types are included in the xanthine oxidase of the present invention. Unless otherwise specified, "xanthine oxidase" in "xanthine oxidase inhibitory activity", "xanthine oxidase inhibitor" and the like also has the same meaning as defined above.

The crystals of the present invention are characterized by powder X-ray diffraction spectrum, solid-state $^{13}$C NMR spectrum, infrared absorption spectrum (KBr method) and/or thermogravimetry/differential thermal analysis (TG/DTA) and the like. The powder X-ray diffraction (XRD) spectrum, solid-state $^{13}$C NMR spectrum and infrared absorption spectrum (KBr method) of these crystals exhibit characteristic patterns, and each crystal has specific diffraction angle 2θ values. In addition, each of these crystals also exhibits its own characteristic thermal behavior in thermogravimetry/differential thermal analysis (TG/DTA).

The crystal form A of the compound (I) has characteristic peaks at diffraction angles of 2θ=8.6°, 10.2°, 13.3°, 14.4°, 18.5°, 19.9°, 21.8°, 25.1°, 25.6°, 26.6°, 27.1° and 29.5° in its powder X-ray diffraction spectrum. In addition, the crystal form A of the compound (I) has a pattern shown in FIG. 1 in its powder X-ray diffraction spectrum.

The crystal form A of the compound (I) has peaks at chemical shifts of 116.3 ppm, 117.6 ppm, 120.0 ppm, 123.6 ppm, 125.9 ppm, 127.4 ppm, 143.7 ppm, 151.8 ppm, 161.1 ppm, 162.3 ppm and 165.5 ppm in its solid-state $^{13}$C NMR spectrum. In addition, the crystal form A of the compound (I) has a pattern shown in FIG. 5 in its solid-state $^{13}$C NMR spectrum.

The crystal form A of the compound (I) has absorption peaks at wave numbers of 745 cm$^{-1}$, 822 cm$^{-1}$, 889 cm$^{-1}$, 975 cm$^{-1}$, 997 cm$^{-1}$, 1611 cm$^{-1}$ and 1705 cm$^{-1}$ in its infrared absorption spectrum (KBr method). In addition, the crystal form A of the compound (I) has a pattern shown in FIG. 8 in its infrared absorption spectrum (KBr method).

The crystal form A of the compound (I) has an exothermic peak at 222° C. in the thermogravimetry/differential thermal analysis (TG/DTA). The crystal form A is an anhydrous crystal.

The crystal form B of the compound (I) has characteristic peaks at diffraction angles of 2θ=10.1°, 12.6°, 13.1°, 14.0°, 18.6°, 24.2°, 25.2°, 25.7°, 27.2° and 30.5° in its powder X-ray diffraction spectrum. In addition, the crystal form B of the compound (I) has a pattern shown in FIG. 2 in its powder X-ray diffraction spectrum.

The crystal form B of the compound (I) has peaks at chemical shifts of 115.4 ppm, 118.0 ppm, 119.8 ppm, 123.2 ppm, 126.4 ppm, 129.1 ppm, 142.7 ppm, 151.2 ppm, 160.9 ppm and 166.6 ppm in its solid-state $^{13}$C NMR spectrum. In addition, the crystal form B of the compound (I) has a pattern shown in FIG. 6 in its solid-state $^{13}$C NMR spectrum.

The crystal form B of the compound (I) has absorption peaks at wave numbers of 744 cm$^{-1}$, 810 cm$^{-1}$, 972 cm$^{-1}$, 997 cm$^{-1}$, 1005 cm$^{-1}$, 1611 cm$^{-1}$ and 1710 cm$^{-1}$ in its infrared absorption spectrum (KBr method). In addition, the crystal form B of the compound (I) has a pattern shown in FIG. 9 in its infrared absorption spectrum (KBr method).

The crystal form B of the compound (I) has an exothermic peak at 225° C. in the thermogravimetry/differential thermal analysis (TG/DTA). The crystal form B is an anhydrous crystal.

The crystal form C of the compound (I) has characteristic peaks at diffraction angles of 2θ=7.2°, 12.5°, 13.0°, 14.7°, 19.2°, 20.0°, 21.4°, 21.7°, 24.7° and 26.0° in its powder X-ray diffraction spectrum. In addition, the crystal form C of the compound (I) has a pattern shown in FIG. 3 in its powder X-ray diffraction spectrum.

The crystal form C of the compound (I) has peaks at chemical shifts of 116.1 ppm, 119.6 ppm, 123.1 ppm, 126.1 ppm, 127.1 ppm, 130.0 ppm, 143.6 ppm, 150.3 ppm, 158.3 ppm, 160.7 ppm, 163.9 ppm, 165.5 ppm and 167.0 ppm in its solid-state $^{13}$C NMR spectrum. In addition, the crystal form C of the compound (I) has a pattern shown in FIG. 7 in its solid-state $^{13}$C NMR spectrum.

The crystal form C of the compound (I) has absorption peaks at wave numbers of 745 cm$^{-1}$, 751 cm$^{-1}$, 809 cm$^{-1}$, 820 cm$^{-1}$, 971 cm$^{-1}$, 1006 cm$^{-1}$, 1613 cm$^{-1}$, 1682 cm$^{-1}$ and 1710 cm$^{-1}$ in its infrared absorption spectrum (KBr method). In addition, the crystal form C of the compound (I) has a pattern shown in FIG. 10 in its infrared absorption spectrum (KBr method).

The crystal form C of the compound (I) has an endothermic peak at 88° C. and an exothermic peak at 225° C. in the thermogravimetry/differential thermal analysis (TG/DTA). The crystal form C is considered to form a solvate with dimethylformamide at a ratio of 1:1.

The crystal form A of the compound (II) has characteristic peaks at diffraction angles of 2θ=7.2°, 10.9°, 13.3°, 15.9°, 18.2°, 20.8°, 22.1°, 25.2°, 26.1° and 29.1° in its powder X-ray diffraction spectrum. In addition, the crystal form A of the compound (II) has a pattern shown in FIG. 4 in its powder X-ray diffraction spectrum, and has an exothermic peak at 281° C. in the thermogravimetry/differential thermal analysis (TG/DTA). The crystal form A is an anhydrous crystal.

As used herein, "characteristic peaks" mean main peaks and unique peaks that are both observed in the powder X-ray diffraction spectrum, $^{13}$C solid-state NMR spectrum, and infrared absorption spectrum (KBr method) of each crystal polymorph. The crystals identified by the diffraction angles of the present invention also include peaks other than those observed as the characteristic peaks described above.

The position and the relative intensity of diffraction angle 2θ in the powder X-ray diffraction spectrum may slightly vary depending on the measurement conditions, and therefore, even if 2θ has a slight difference, the identity of a crystal form should be recognized by appropriately referring to the pattern of the entire spectrum. Crystals within the range of such errors are also included in the present invention. The errors in 2θ may be, for example, in the range of ±0.5° or ±0.2°. In other words, the crystals identified by the above diffraction angles also include those having diffraction angles within the error range of ±0.5° or ±0.2°.

Generally, errors may arise also in chemical shifts in solid-state $^{13}$C NMR spectrum. Such errors are in the range, for example, of ±0.25 ppm, and typically ±0.5 ppm. In other words, the crystals identified by the above chemical shifts also include those having chemical shifts within the error range of ±0.25 ppm or ±0.5 ppm.

Generally, errors may arise also in absorption peaks in infrared absorption spectrum (KBr method). Such errors are in the range, for example, of ±2 cm$^{-1}$, and typically ±5 cm$^{-1}$. In other words, the crystals identified by the above wave numbers also include those having wave numbers within the error range of ±2 cm$^{-1}$ or ±5 cm$^{-1}$.

In the thermogravimetric/differential thermal analysis (TG/DTA), an "exothermic peak" and an "endothermic peak" are defined as the temperature at the starting point of a peak and mean the exothermic and endothermic starting temperature determined by extrapolation. The exothermic peak" and "endothermic peak" in the TG/DTA may vary a little depending on the measurement conditions. For example, the error is considered to be in the range of ±5° C. or ±2° C. In other words, the crystals identified by the above peaks also include those having peaks within the error range of ±5° C. or ±2° C.

Further, for powder X-ray diffraction spectrum, solid-state $^{13}$C NMR spectrum, infrared absorption spectrum (KBr method) and TG/DTA, the difference between the measured values for a reference material of crystals, for example, each crystal obtained by the method described in the present examples and the numerical values described in the present application may be accepted as the measurement errors. That is, the crystals that have the same diffraction angles, chemical shifts, infrared absorption peaks or exothermic and endothermic peaks within the range of errors determined by such methods are included in the crystals of the present invention.

A crystal form A of the compound (I) is produced by a method, comprising the steps of:

suspending an alkyl ester of the compound (I) in a solvent and performing hydrolysis by adding an aqueous solution of a base thereto; and neutralizing the reaction product.

In addition, the method of producing the crystal form A of the compound (I) may further comprise a step of adding water to the neutralized substance and a subsequent step of stirring the reaction solution.

The solvent used for suspending an alkyl ester of the compound (I) includes, for example, aromatic hydrocarbons such as benzene, toluene and xylene; ethers such as diethyl ether, tetrahydrofuran (THF), 1,4-dioxane, 1,2-dimethoxy ethane, 1,2-diethoxy ethane and methyl tert-butyl ether; halogenated hydrocarbons such as dichloromethane, 1,2-dichloroethane and chloroform; alcohols such as methanol, ethanol, 2-propanol butanol, hexafluoro-2-propanol and trifluoroethanol; N,N-dimethylformamide (DMF); N,N-dimethylacetamide (DMA); N-methylpyrrolidone; dimethyl sulfoxide (DMSO); acetonitrile; acetone; ethyl acetate; and water, and a mixed solvent thereof. A preferred solvent is an ether or an alcohol, water or a mixed solvent thereof.

Examples of an alkyl ester of the compound (I) preferably include an alkyl ester having 1 to 6 carbon atoms and more preferably an ethyl ester. Here, an alkyl ester refers to a linear or branched aliphatic saturated hydrocarbon ester. Specific examples of an alkyl ester having 1 to 6 carbon atoms include a methyl ester, an ethyl ester, an isopropyl ester and a t-butyl ester.

The hydrolysis reaction of the alkyl ester of the compound (I) to the compound (I) proceeds by suspending the alkyl ester of compound (I) in the solvent mentioned above (for example, in an amount of 15 times the amount of the alkyl ester) and then subjecting the suspension to a reaction with a base in an equivalent or slightly excessive amount relative to the alkyl ester. Examples of preferred bases include sodium hydroxide, potassium hydroxide and lithium hydroxide. The reaction proceeds in the range between 0° C. and 100° C. and is performed preferably in the range between 20° C. and 30° C.

After the hydrolysis reaction, the reaction product is neutralized by reacting the base used with an acid in an equivalent or slightly excessive amount relative to the base used. An example of a preferred acid includes hydrochloric acid. The neutralization reaction proceeds in the range between 0° C. and 100° C. and is performed preferably in the range between 0° C. and 30° C.

Subsequently, water (for example, in an amount of 5 times the amount of the alkyl ester) is added to the neutralized reaction product and the mixture is stirred for one hour, and then the precipitate is filtered out and dried to obtain crystals. Although the amount of the solvent, the amount of water added, stirring conditions and the time until separation by filtering are not particularly limited, since these conditions may have an influence on the yield of crystals, chemical purity, particles diameter and particle size distribution, these conditions are preferably combined and set according to the purpose. The filtration can be performed by using a usual method, for example, natural filtration, pressure filtration, vacuum filtration, or centrifuge separation. The drying can be performed by using a usual method, for example, natural drying, vacuum drying, heating drying and vacuum heating drying can be used.

An alkyl ester of the compound (I) may be synthesized by any one of methods, for example, by the following methods.

Synthesis of Compound (A-2)

[Chem. 1]

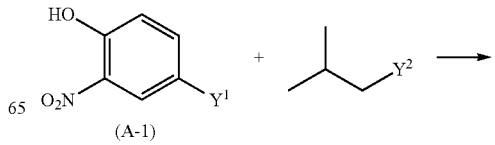

(A-1)

-continued

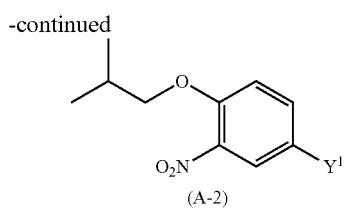

(wherein Y¹ and Y² represent a leaving group.)

Examples of a leaving group represented by Y¹ and Y² include a halogen atom, a methanesulfonyloxy group, a p-toluenesulfonyloxy group, a trifluoromethanesulfonyloxy group and the like. The reaction is a method for synthesizing compound (A-2) by a reaction of an alkylating reagent having a leaving group with a phenolic hydroxyl group in a compound (A-1) in the presence of a base. Examples of the base to be used include an inorganic salt such as sodium hydride, sodium hydroxide, potassium hydroxide, lithium hydroxide, sodium carbonate, potassium carbonate, cesium carbonate; a metal alkoxide such as sodium ethoxide, sodium methoxide and potassium t-butoxide; and an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting the compound (A-1) with a base in an equivalent or slightly excessive amount relative to the compound (A-1) in a solvent inactive to the reaction in the range between 0° C. and 140° C., subsequently adding an alkylating reagent in an equivalent or excessive amount relative to the compound (A-1), and reacting generally for 0.5 to 16 hours. The reaction is preferably performed under an inert gas atmosphere such as nitrogen. Here, the solvent includes, though not particularly limited, for example, ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); water; and a mixed solvent thereof.

Synthesis of Compound (A-4)

[Chem. 2]

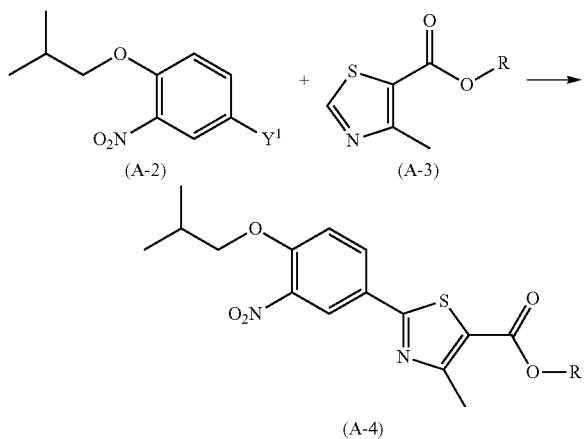

(wherein R represents an alkyl group having 1 to 6 carbon atoms.)

The synthesis method is a method for synthesizing compound (A-4) by coupling compounds (A-2) and (A-3) together. Examples of a leaving group represented by Y¹ include a halogen atom, a methanesulfonyloxy group, a p-toluenesulfonyloxy group and a trifluoromethanesulfonyloxy group. The reaction is performed by reacting the compounds (A-2) and (A-3) using an equivalent or excessive amount of one compound relative to the other in a solvent inactive to the reaction in the presence of a base and a transition metal catalyst, by adding a ligand, a carboxylic acid and a monovalent or divalent copper salt when necessary, in the range between room temperature and a reflux temperature generally for 0.5 hours to 2 days. The reaction is preferably performed under an inert gas atmosphere such as nitrogen. Here, the solvent includes, though not particularly limited, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; and a mixed solvent thereof. Examples of the base include lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate and potassium acetate; a metal salt of an alkoxide having 1 to 6 carbon atoms (lithium salt, sodium salt, potassium salt and magnesium salt); a metal salt of an alkyl anion having 1 to 6 carbon atoms (lithium salt, sodium salt, potassium salt and magnesium salt); tetra (alkyl having 1 to 4 carbon atoms) ammonium salt (fluoride, chloride and bromide); diisopropylethylamine; tributylamine; N-methylmorpholine; diazabicycloundecene; diazabicylcooctane; and imidazole. Examples of the transition metal catalyst include copper, palladium, cobalt, iron, rhodium, ruthenium and iridium. Examples of the ligand include tri(t-butyl)phosphine, tri(cyclohexyl)phosphine, t-butyldicyclohexylphosphine, di(t-butyl)cyclohexylphosphine and di(t-butyl)methylphosphine. Examples of the monovalent or divalent copper salt include copper chloride (I), copper bromide (I), copper iodide (I), copper acetate (I), copper fluoride (II), copper chloride (II), copper bromide (II), copper iodide (II), copper acetate (II), a hydrate thereof and a mixture thereof. Examples of the carboxylic acid include formic acid, acetic acid, propionic acid, n-butyric acid, isobutyric acid, pentanoic acid, isopentanoic acid, pivalic acid and trifluoroacetic acid.

Synthesis of Compound (A-5)

[Chem. 3]

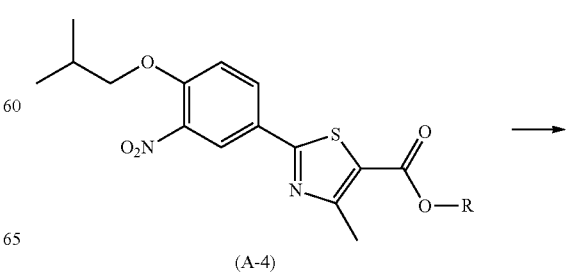

-continued

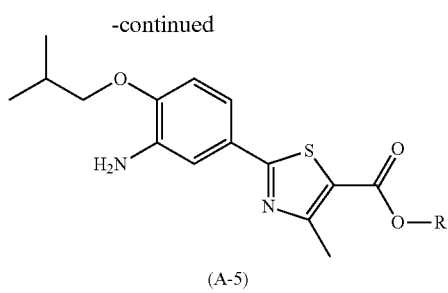

(A-5)

(wherein R represents an alkyl group having 1 to 6 carbon atoms.)

The synthesis method is a method for synthesizing a compound (A-5) by the reduction of a nitro group of the compound (A-4). The reaction is performed by reacting the compound (A-4) under a hydrogen gas atmosphere in a solvent inactive to the reaction in the presence of a transition metal catalyst in the range between room temperature and a reflux temperature generally for 0.5 hours to 2 days. Here, the solvent includes, though not particularly limited, for example, aromatic hydrocarbons such as benzene, toluene and xylene; ethers such as diethyl ether, tetrahydrofuran 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); ethyl acetate; and a mixed solvent thereof. Preferred examples of the transition metal catalyst include palladium-carbon, palladium hydroxide, palladium black, platinum-carbon, Raney nickel and the like.

Synthesis of Compound (A-6)

[Chem. 4]

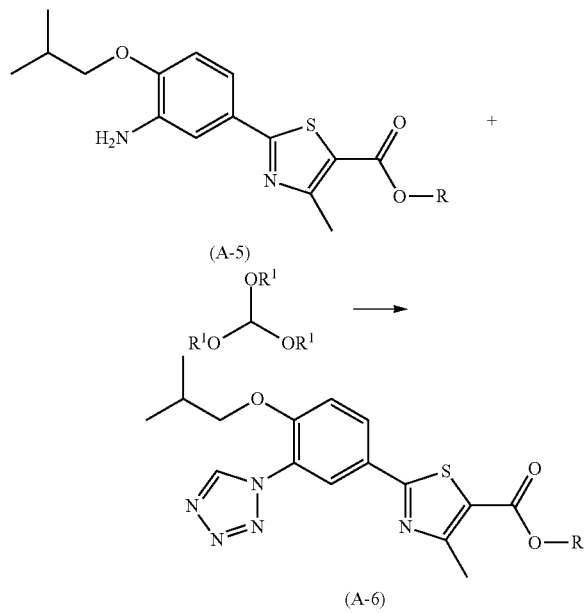

(wherein R and $R^1$ independently represent an alkyl group having 1 to 6 carbon atoms.)

The synthesis method is a method for synthesizing a tetrazole ring by reacting the compound (A-5) with an orthoformate and an azide compound. The reaction is performed by reacting the compound (A-5), an orthoformate and an azide compound using an equivalent or excessive amount of one of the compounds relative to the other in a solvent inactive to the reaction in the presence of an acid in the range between room temperature and a reflux temperature generally for 0.5 hours to 2 days. The reaction is preferably performed under an inert gas atmosphere such as nitrogen. Examples of the orthoformate include trimethyl orthoformate and triethyl orthoformate. In addition, examples of the azide compound include sodium azide and trimethyl silylazide. Examples of the acid to be used include an organic acid such as formic acid and acetic acid, an inorganic acid such as hydrochloric acid and sulfuric acid, and a Lewis acid such as indium triflate, ytterbium triflate, zinc triflate and trichloroindium. The solvent to be used for these reactions includes, though not particularly limited, for example, benzene, toluene, dichloromethane, dichloroethane, chloroform, carbon tetrachloride, diethyl ether, tetrahydrofuran (THF), 1,4-dioxane, 1,2-dimethoxy ethane, 1,2-diethoxy ethane, N,N-dimethylformamide (DMF), N-methylpyrrolidone, dimethyl sulfoxide (DMSO) and a mixed solvent thereof, and an acid such as acetic acid may also be used as a solvent.

Intermediate compounds of the reaction can be purified by a usual method such as recrystallization, reprecipitation and various chromatography methods, if necessary, during the synthesis process.

A crystal B of the compound (I) can be produced by a method comprising a step of suspending a crystal A of the compound (I) in a solvent.

In addition, a method of producing the crystal B of the compound (I) may further comprise a step of subsequently heating the reaction solution.

In the production of the crystal B of the compound (I), examples of the solvent for suspending the crystal. A include: aromatic hydrocarbons such as benzene, toluene and xylene; ethers such as diethyl ether, tetrahydrofuran (THF), 1,4-dioxane, 1,2-dimethoxyethane, 1,2-diethoxyethane and methyl tert-butyl ether; ketones such as acetone and 2-butanone, esters such as ethyl acetate and isobutyl acetate; halogenated hydrocarbons such as dichloromethane, 1,2-dichloroethane and chloroform; alcohols such as methanol, ethanol, 2-propanol, butanol, hexafluoro-2-propanol and trifluoroethanol; N,N-dimethylformamide (DMF); N,N-dimethylactamide (DMA); N-methylpyrrolidone; dimethylsulfoxide (DMSO); acetonitrile; acetone; ethyl acetate; methyl ethyl ketone; water; or a mixed solvent thereof. Preferred examples of the solvent include ethers, ketones, esters, alcohols, water or a mixed solvent thereof.

The conversion of the crystal A of the compound (I) into the crystal B of the compound (I) proceeds by suspending the crystal A of the compound (I) in the above solvent (for example, 5 to 60 times the amount of the crystal A of the compound (I)) and then heating under reflux the reaction solution for 6 hours.

Subsequently, after stirring the reaction solution at 25° C., the precipitate is filtered out and dried to obtain crystals. Although the amount of the solvent, heating time stirring conditions and the time until separation by filtering are not particularly limited, since these conditions may have an influence on the yield of crystals, chemical purity, particle diameter and particle size distribution, these conditions are preferably combined and set according to the purpose. The filtration can be performed by using a usual method, for example, natural filtration, pressure filtration, vacuum filtration, or centrifuge separation. The drying can be performed by using a usual method, for example, natural drying, vacuum drying, heating drying and vacuum heating drying.

A crystal C of the compound (I) is obtained by crystallizing the compound (I) using N,N-dimethylformamide solvent.

A reaction solution is prepared by adding N,N-dimethylformamide (for example, 10 times the amount of the compound (I)) to the compound (I) and dissolving the mixture by heating and stirring at 80° C. The reaction solution is cooled to the range between 20° C. and 30° C. and stirred for two hours. The precipitate is filtered out, and the filtered product is washed with ethanol (for example, using 10 times the amount of the compound (I)). The mother liquid is allowed to stand in the range between 20° C. and 30° C. for 7 days and the precipitate is filtered out and dried to obtain crystals. Although the solvent, stirring conditions and the time until separation by filtering are not particularly limited, since these conditions may have an influence on the yield of crystals, chemical purity, particle diameter and particle size distribution, these conditions are preferably combined and set according to the purpose. The filtration can be performed by using a usual method, for example, natural filtration, pressure filtration, vacuum filtration, or centrifuge separation. The drying can be performed by using a usual method, for example, natural drying, vacuum drying, heating drying and vacuum heating drying.

A crystal C of the compound (I) can be produced by a method comprising a step of suspending a crystal B of the compound (I) in a solvent.

A mixed solution (for example, 10 times the amount of the compound (I)) of N,N-dimethylformamide and ethyl acetate in a ratio of 1:1 is added to the crystal B of the compound (I), followed by stirring at room temperature for 14 days. The resulting solution is filtered and the filtered product is dried at room temperature to obtain crystals. Although the solvent, stirring conditions and the time until separation by filtering are not particularly limited, since these conditions may have an influence on the yield of crystals, chemical purity, particle diameter and particle size distribution, these conditions are preferably combined and set according to the purpose. The filtration can be performed by using a usual method, for example, natural filtration, pressure filtration, vacuum filtration, or centrifuge separation. The drying can be performed by using a usual method, for example, natural drying, vacuum drying, heating drying and vacuum heating drying.

The compound (I) can be produced, for example, by the following method.

[Chem. 5]

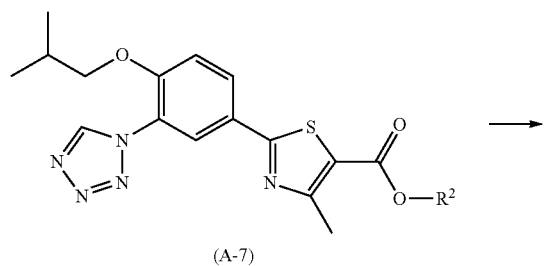

(A-7)

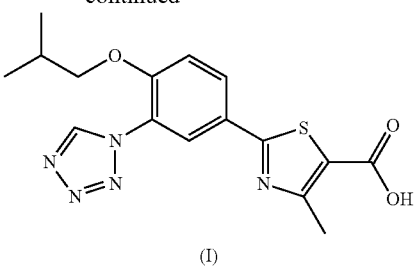

(I)

(wherein $R^2$ represents a protective group of a carboxyl group.)

The synthesis method is a method for synthesizing a compound (I) by deprotecting a protective group $R^2$ of the compound (A-7) using an acid, a base or the like. The term "a protective group of a carboxyl group" is, for example, a general protective group of a carboxyl group, which is described in PROTECTIVE GROUPS in ORGANIC SYNTHESIS, THIRD EDITION, H John Wiley & Sons, Inc. and examples of the protective group include methyl group, ethyl group, isopropyl group, heptyl group, t-butyl group, methoxymethyl group, methylthiomethyl group, methoxyethoxymethyl group, methoxyethyl group, benzyl group and the like. The compound (A-7) can be synthesized by a method in which R is replaced by $R^2$ in the synthesis method of the compound (A-6). The reaction is performed by reacting the compound (A-7) with an equivalent or excessive amount of an acid or a base relative to the compound in a solvent inactive to the reaction in the range between room temperature and a reflux temperature generally for 0.5 hours to 5 days. Here, the solvent includes, though not particularly limited, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid or a solution obtained by diluting these acids with water or an organic solvent. Examples of the base include an inorganic base such as sodium hydroxide, potassium hydroxide, lithium hydroxide, sodium carbonate and potassium carbonate; a metal alkoxide such as sodium ethoxide and sodium methoxide; or a solution obtained by diluting these bases with water or an organic solvent. When a base is used for deprotecting, the compound (I) is obtained by adding an acid to the reaction solution and neutralize it. The above exemplified acids can be used for the neutralization. The compound (I) obtained can be purified by a usual method such as recrystallization, reprecipitation and various chromatography methods, if necessary.

A crystal A of the compound (II) can be produced, for example, by the following method.

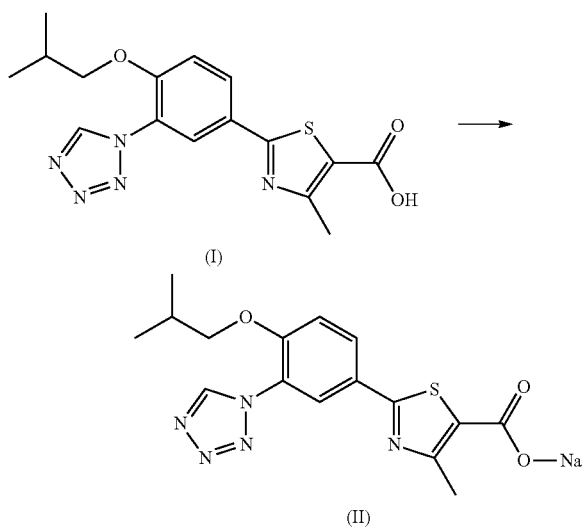

(I)

(II)

The compound (II) can be produced by a method comprising a step of suspending the compound (I) in a solvent and adding sodium hydroxide. In addition, the method may further comprise a step of stirring the reaction solution. The solvent for suspending the compound (I) includes, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Preferred solvents are ethers or alcohols, water or a mixed solvent thereof. The salt, formation reaction from the compound (I) to the compound (II) proceeds by suspending the compound (I) in the solvent mentioned above (for example, 10 times the amount of the carboxylic acid) and then reacting the compound (I) with an equivalent or a slightly excessive amount, of sodium hydroxide relative to the compound (I). The reaction proceeds in the range between 0° C. and 100° C., but it is preferably carried out in the range between 0° C. and 30° C.

Subsequently, the mixture is stirred for one hour, and then the precipitate is filtered out and dried to obtain crystals. Although the amount of the solvent, the amount of water added, stirring conditions and the time until separation by filtering are not particularly limited, since these conditions may have an influence on the yield of crystals, chemical purity, particle diameter and particle size distribution, these conditions are preferably combined and set according to the purpose. The filtration can be performed by using a usual method, for example, natural filtration, pressure filtration, vacuum filtration, or centrifuge separation. The drying can be performed by using a usual method, for example, natural drying, vacuum drying, heating drying and vacuum heating drying.

Intermediate compounds of the reaction can be purified by a usual method such as recrystallization, reprecipitation and various chromatography methods, if necessary, during the synthesis process.

Although the crystals of the present invention can be identified by a characteristic powder X-ray diffraction spectrum, solid-state $^{13}C$ NMR spectrum, infrared absorption spectrum (KBr method) or thermogravimetric/differential thermal analysis (TG/DTA), when other crystal forms are present, the incorporation rate thereof is not referred to. When only a specific form of crystal is obtained, at least the incorporation of the other crystal forms may be accepted to a degree that cannot be detected by these methods of measurement. In addition, when a specific form of crystal is used as an active pharmaceutical ingredient for a pharmaceutical agent, it does not mean that the inclusion of the other forms of crystals is unacceptable.

The each crystal of the present invention can be used as a pharmaceutical active ingredient. In addition, not only one form of crystals but also a mixture of two or more forms of crystals can be used.

In the present invention, the crystals of the compound (I) and the compound (II) are more advantageous than those that are non-crystalline in the handleability during production, reproducibility, stability and storage stability.

A pharmaceutical composition can be obtained by using the crystal of the compound (I), or the compound (II) or the crystal thereof in the present invention, and a pharmaceutically acceptable carrier.

A preparation containing the crystal of the compound (I), or the compound (II) or the crystals thereof in the present invention is prepared using additives usually used for formulation. Examples of the additives for a solid preparation include an excipient such as lactose, saccharose, glucose, corn starch, white potato starch, crystalline cellulose, light anhydrous silicic acid, synthetic aluminum silicate, magnesium aluminometasilicate and calcium hydrogen phosphate; a binder such as crystalline cellulose, carboxymethyl cellulose, hydroxypropyl cellulose, carboxymethylcellulose sodium and polyvinyl pyrrolidone; a disintegrating agent such as starch, carboxymethylcellulose sodium, carboxymethylcellulose calcium, croscarmellose sodium and sodium carboxymethyl starch; a lubricant such as talc and stearic acid; a coating agent such as hydroxymethylpropylcellulose, hydroxypropylmethylcellulose phthalate and ethylcellulose; and a coloring agent, the additives for a semisolid preparation include a substrate such as white petrolatum, and the additives for a liquid preparation include a solvent such as ethanol; a solubilizing agent such as ethanol; a preservative such as para-hydroxybenzoate; a tonicity agent such as glucose; a buffering agent such as citric acid; an antioxidant such as L-ascorbic acid; a chelating agent such as EDTA; and a suspending agent and an emulsifying agent such as polysorbate 80.

The crystal of the compound (I), or the compound (II) or the crystals thereof in the present invention can be used in any dosage forms such as a solid preparation, a semisolid preparation and a liquid preparation, and used in a preparation for any form of administration such as an oral preparation and a parenteral preparation (such as an injection preparation, a percutaneous preparation, an ophthalmic preparation, a suppository preparation, a transnasal preparation and an inhalation preparation).

A pharmaceutical composition containing the crystal of the compound (I), or the compound (II) or the crystals thereof in the present invention as an active ingredient can be used as a xanthine oxydase inhibitor, or a therapeutic agent or a prophylactic agent for diseases associated with xanthine oxidase such as gout, hyperuricemia, tumor lysis syndrome, urinary calculi, hypertension, dyslipidemia, diabetes, cardiovascular diseases such as arteriosclerosis and heart failure, kidney diseases such as diabetic nephropathy, respiratory diseases such as chronic obstructive pulmonary disease, inflammatory bowel diseases or autoimmune diseases. Here, the term "prophylactic" means to prevent the incidence or onset of diseases in an individual who is not affected by diseases or has not yet developed diseases and the term "therapeutic" means to treat, suppress or remedy diseases or symptoms in an individual who has already been affected by diseases or has developed diseases.

EXAMPLES

[Measurement Method]
The powder X-ray diffraction of the crystals of the present invention was measured under the following conditions.
Apparatus: D8 DISCOVER with GADDS CS manufactured by Bruker AXS
Radiation source: Cu Kα, Wavelength: 1.541838 ($10^{-10}$ m), 40 kV-40 mA, Incident flat plate graphite monochromator, collimator diameter 300 μm, two-dimensional PSPC detector, scan 3 to 40°
[Measurement Method]
The solid-state $^{13}$C NMR spectrum of the crystals of the invention was measured under the following conditions.
Apparatus: DSX300WB manufactured by Bruker
Measurement nucleus: 13C
Pulse repetition rate: 5 seconds
Pulse mode: CP/MAS measurement
[Measurement Method]
The infrared absorption method (KBr method) of the crystals of the present invention was measured under the following conditions according to the potassium bromide tablet method of the infrared absorption method described in general test methods of Japanese Pharmacopoeia.
Apparatus: AVATAR 320 manufacture by ThermoFischer Scientific
Measurement range: 4000 to 400 $cm^{-1}$
Resolution: 4 cm:
Number of integration: 64
The thermogravimetric/differential thermal analysis (TG/DTA) of the crystals of the present invention was performed under the following conditions.
Apparatus: TG8120 manufactured by Rigaku
Temperature elevation rate: 10° C./min, Atmosphere: nitrogen, Sample pan: aluminum, Reference: alumina, Sampling: 1.0 sec., Measurement temperature range: 25 to 300° C.
As for the compounds for which $^1$H-NMR spectrum (400 MHz, DMSO-$d_6$ or CDCl$_3$) was measured, the chemical shift (δ: ppm) and coupling constant (J: Hz) are shown.
Apparatus: JMTC-400/54/SS manufactured by JEOL
The abbreviations represent the followings:
s=singlet, d=doublet, t=triplet, q=quartet, brs=broad singlet, m=multiplet Reference Example 1

Synthesis of ethyl 4-methyl-2-[4-(2-methylpropoxy)-3-(1H-1,2,3,4-tetrazol-1-yl)phenyl]-1,3-thiazole-5-carboxylate (1) To a mixture prepared by suspending 20.0 g of 4-bromo-2-nitrophenol and 19.0 g of potassium carbonate in 200 mL of N,N-dimethylformamide, with 20.1 g of isobutyl bromide was added and the resultant mixture was heated at 110° C. for 22 hours under a nitrogen atmosphere. Subsequently, after the addition of water to the reaction mixture solution, extraction was performed using ethyl acetate. The organic layer was washed with a saline solution, followed by drying and concentration under reduced pressure to obtain 24.8 g of 4-bromo-1-(2-methylpropoxy)-2-nitrobenzene.

(2) A mixture prepared by adding 2.10 g of potassium bicarbonate, 43.5 mg of palladium chloride (II) and 205 mg of copper bromide (I) to 2.74 g of 4-bromo-1-(2-methylpropoxy)-2-nitrobenzene was suspended in 35 mL of toluene. Subsequently, a reaction mixture solution prepared by adding 2.05 g of ethyl 4-methyl-1,3-thiazole-5-carboxylate, 92 μL of isobutyric acid and 230 μL of di-t-butylcyclohexylphosphine to the suspension was heated at 120° C. for 14 hours under a nitrogen atmosphere. The reaction mixture solution was celite-filtered to remove insoluble matter, water was added to the filtrate, and extraction was performed using ethyl acetate. The organic layer was washed with a saline solution and then subjected to drying and concentration under reduced pressure, followed by purifying by a conventional method to obtain 3.16 g of ethyl 4-methyl-2-[3-nitro-4-(2-methylpropoxy)phenyl]-1,3-thiazole-5-carboxylate.
$^1$H-NMR (400 MHz, CDCl3) δ:1.07 (6H, d, J=6.8 Hz), 1.39 (3H, t, 6.8 Hz), 2.14-2.22 (1H, m), 2.77 (3H, s), 3.92 (2H, d, J=6.0 Hz), 4.36 (2H, q, J=6.8 Hz), 7.12 (1H, d, J=8.8 Hz), 8.09 (1H, dd, J=2.0, 8.8 Hz), 8.43 (1H, d, J=2.0 Hz)

(3) A reaction mixture solution was prepared by suspending 3.16 g of ethyl 4-methyl-2-[3-nitro-4-(2-methylpropoxy)phenyl]-1,3-thiazole-5-carboxylate in 30 mL of ethanol, and adding 200 mg of palladium/carbon (10 wt %) to the suspension, and the reaction mixture was stirred at 50° C. for 14 hours under a hydrogen atmosphere. The reaction mixture solution was filtered and the filtrate was concentrated under reduced pressure to obtain 2.12 g of ethyl 2-[3-amino-4-(2-methylpropoxy)phenyl]-4-methyl-1,3-thiazole-5-carboxylate.

(4) A reaction mixture solution prepared by suspending 2.12 g of ethyl 2-[3-amino-4-(2-methylproxy)phenyl]-4-methyl-1,3-thiazole-5-carboxylate in 20 mL of acetic acid and adding 780 mg of sodium azide and 1.78 g of triethyl orthoformate was heated at 70° C. for 2 hours under a nitrogen atmosphere. After cooling the reaction mixture to room temperature, 20 ml of water was added, followed by purifying by a conventional method to obtain 2.25 g of ethyl 4-methyl-2-[4-(2-methylpropoxy)-3-(1H-1,2,3,4-tetrazol-1-yl)phenyl]-1,3-thiazole-5-carboxylate.
$^1$H-NMR (400 MHz, CDCl3) δ:1.02 (6H, d, J=6.8 Hz), 1.40 (3H, t, J=6.8 Hz), 2.10-2.17 (1H, m), 2.78 (3H, s), 3.95 (2H, d, J=6.8 Hz), 4.36 (2H, q, J=6.8 Hz), 7.18 (1H, d, J=8.8 Hz), 8.07 (1H, dd, J=2.4, 8.8 Hz), 8.46 (1H, d, J=2.8 Hz), 9.21 (1H, s)

Example 1

Production of crystal Form A of 4-methyl-2-[4-(2-methylpropoxy)-3-(1H-1,2,3,4-tetrazol-1-yl)phenyl]-1,3-thiazole-5-carboxylic Acid: Compound (1)

Figure 5:
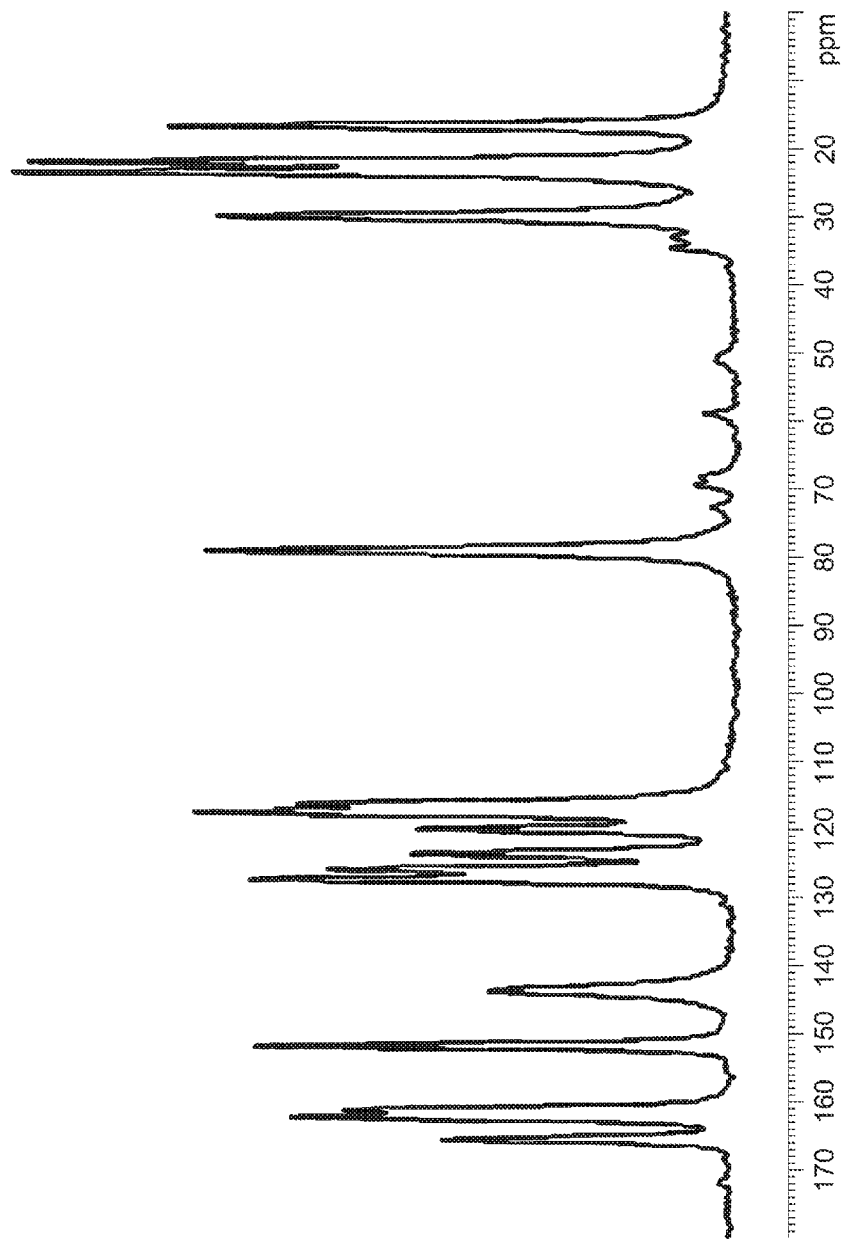
FIG. 5 is a solid-state $^{13}$C NMR spectrum of crystal form A of the compound (I).
Figure 8:
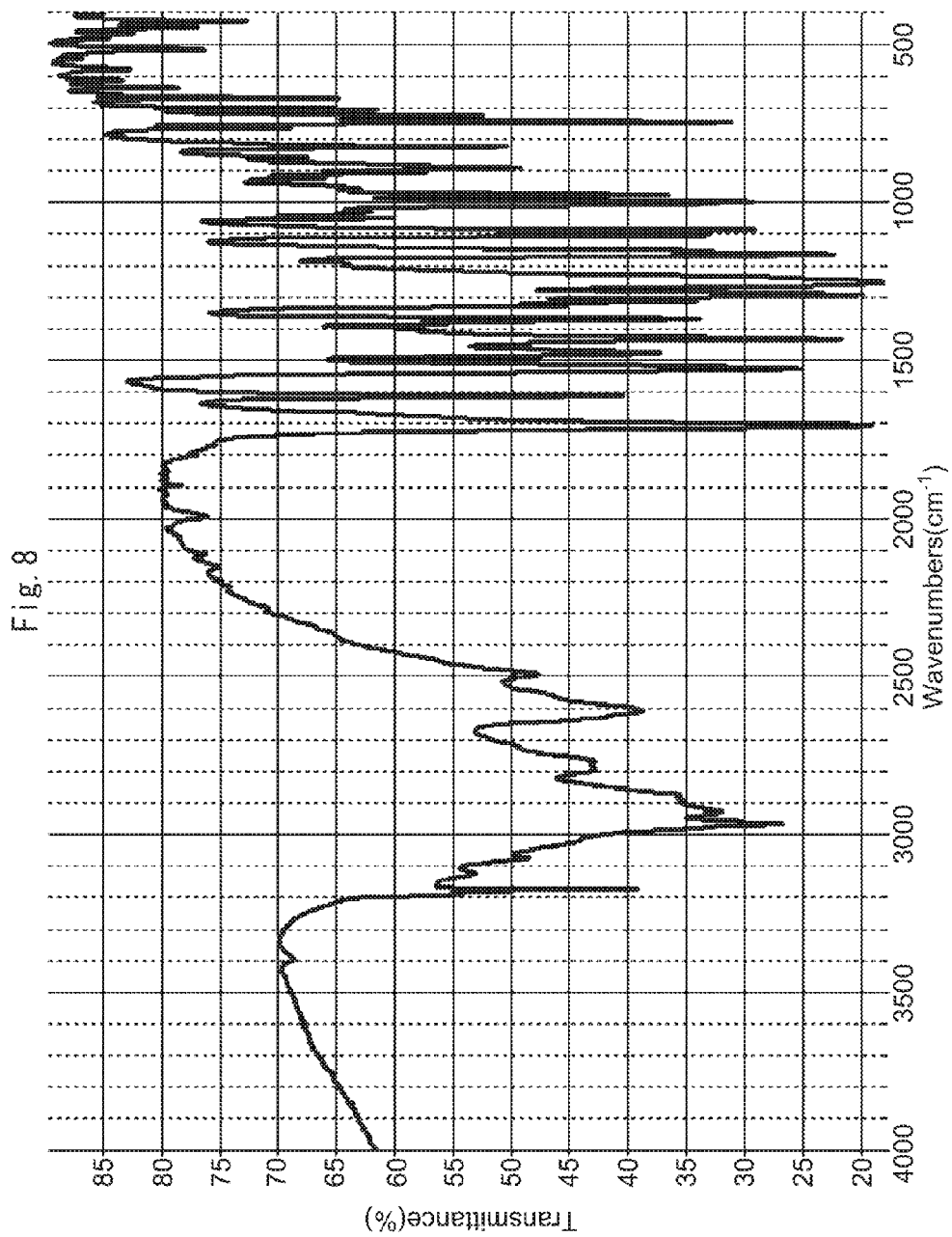
FIG. 8 is an infrared absorption spectrum (KBr method) of crystal form A of the compound (I).

A reaction mixture solution prepared by dissolving 883 g of ethyl 4-methyl-2-[4-(2-methylpropoxy)-3-(1H-1,2,3,4-tetrazol-1-yl)phenyl]-1,3-thiazole-5-carboxylate in 13.2 L of a mixed solution of tetrahydrofuran/methanol=1/1 and by adding 2.28 L of 2 M sodium hydroxide aqueous solution to the mixture was stirred in the range between 20° C. and 30° C. for 3 hours. While stirring in the range between 20° C. and 30° C., 2.28 L of 2 M hydrochloric acid is slowly added to the reaction mixture solution and further 4.4 L of water was slowly added. The reaction mixture solution was stirred in the range between 20° C. and 30° C. for one hour and crystals were obtained by filtration. The resulting crystals were washed with 4.4 L of a mixed solution of methanol/ water=1/1 and 4.4 L of water. The crystals were vacuum dried at 50° C. to yield 811 g of crystals of 4-methyl-2-[4-(2-methylpropoxy)-3-(1H-1,2,3,4-tetrazol-1-yl)phenyl]-1,3-thiazole-5-carboxylic acid. The XRD of the resultant crystals is shown in FIG. 1. Peaks were observed at diffraction angles of 2θ=8.6°, 10.2°, 13.3°, 14.4°, 18.5°, 19.9°, 21.8°, 25.1°, 25.6°, 27.1° and 29.5°. The solid-state $^{13}$C NMR spectrum of the resultant crystals is shown in FIG. 5. Peaks were observed at chemical shifts of 116.3 ppm, 117.6 ppm, 120.0 ppm, 123.6 ppm, 125.9 ppm, 127.4 ppm, 143.7 ppm, 151.8 ppm, 161.1 ppm, 162.3 ppm and 165.5 ppm. The infrared absorption spectrum (KBr method) of the resultant crystals is shown in FIG. 8. Peaks were observed at wave numbers of 745 cm$^{-1}$, 822 cm$^{-1}$, 889 cm$^{-1}$, 975 cm$^{-1}$, 997 cm$^{-1}$, 1611 cm$^{-1}$ and 1705 cm$^{-1}$. In addition, an exothermic peak in thermogravimetry/differential thermal analysis (TG/DTA) was observed at 222° C.

$^1$H-NMR (400 MHz, DMSO-d6) δ:0.85 (6H, d, J=6.8 Hz), 1.93-2.00 (1H, m), 2.66 (3H, s), 3.96 (2H, d, J=6.0 Hz), 7.48 (1H, d, J=8.8 Hz), 8.18 (1H, dd, J=2.4, 8.8 Hz), 8.27 (1H, d, J=2.4 Hz), 9.79 (1H, s), 13.41 (1H, s)

Example 2

Production of Crystal Form B of 4-methyl-2-[4-(2-methylpropoxy)-3-(1H-1,2,3,4-tetrazol-1-yl)phenyl]-1,3-thiazole-5-carboxylic Acid: Compound (I)

Figure 2:
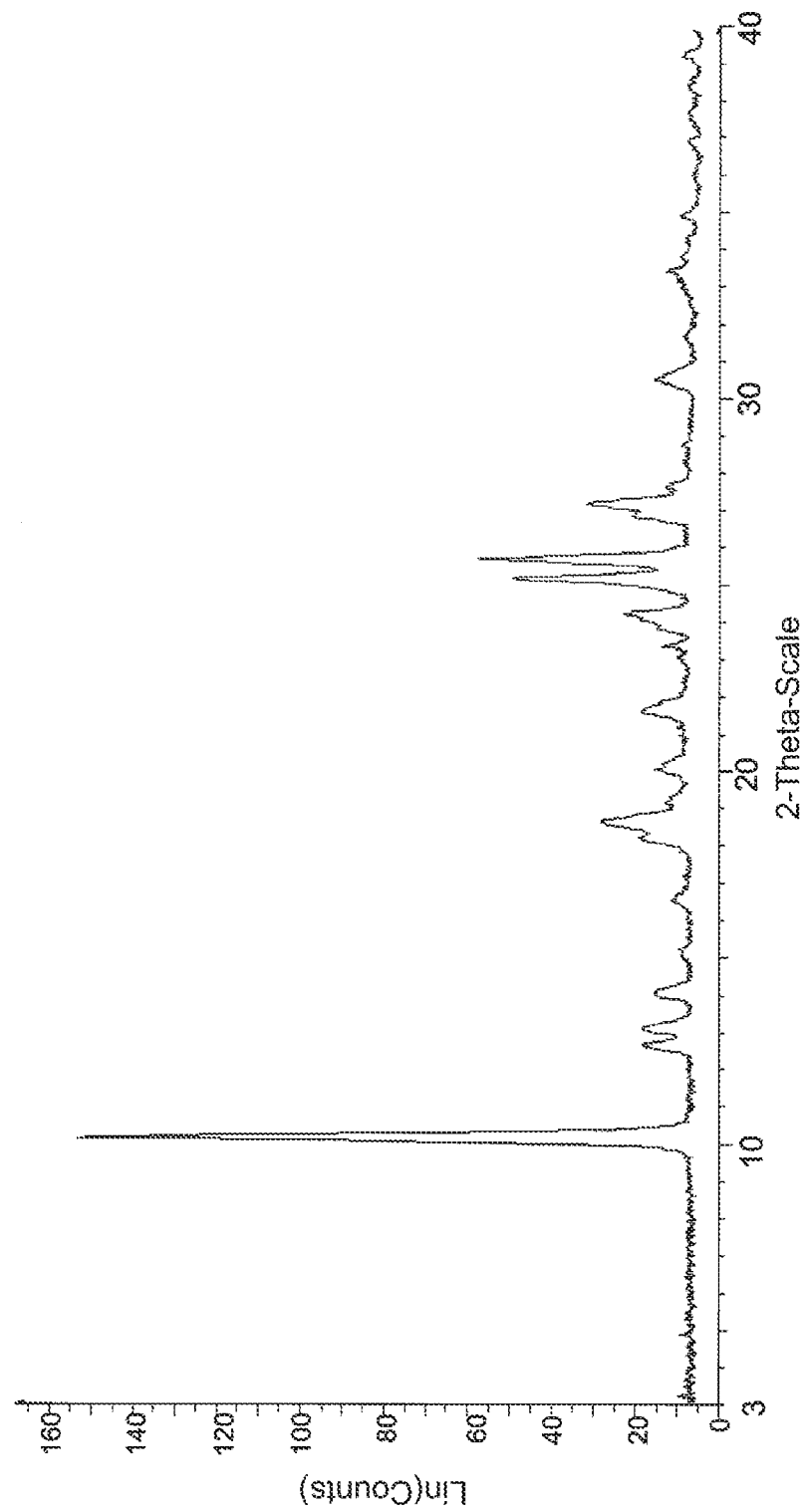
FIG. 2 is a powder X-ray diffraction spectrum of crystal form B of the compound (I).
Figure 6:
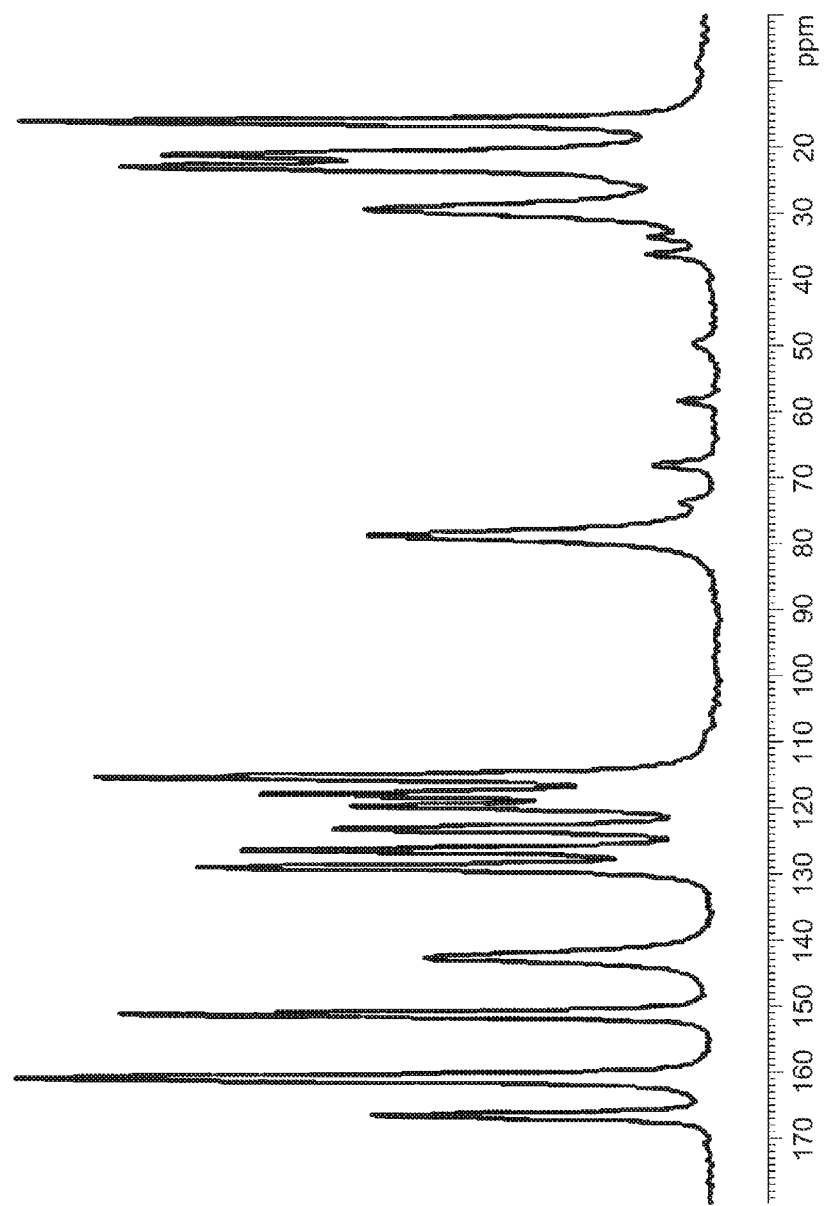
FIG. 6 is a solid-state $^{13}$C NMR spectrum of crystal form B of the compound (I).
Figure 9:
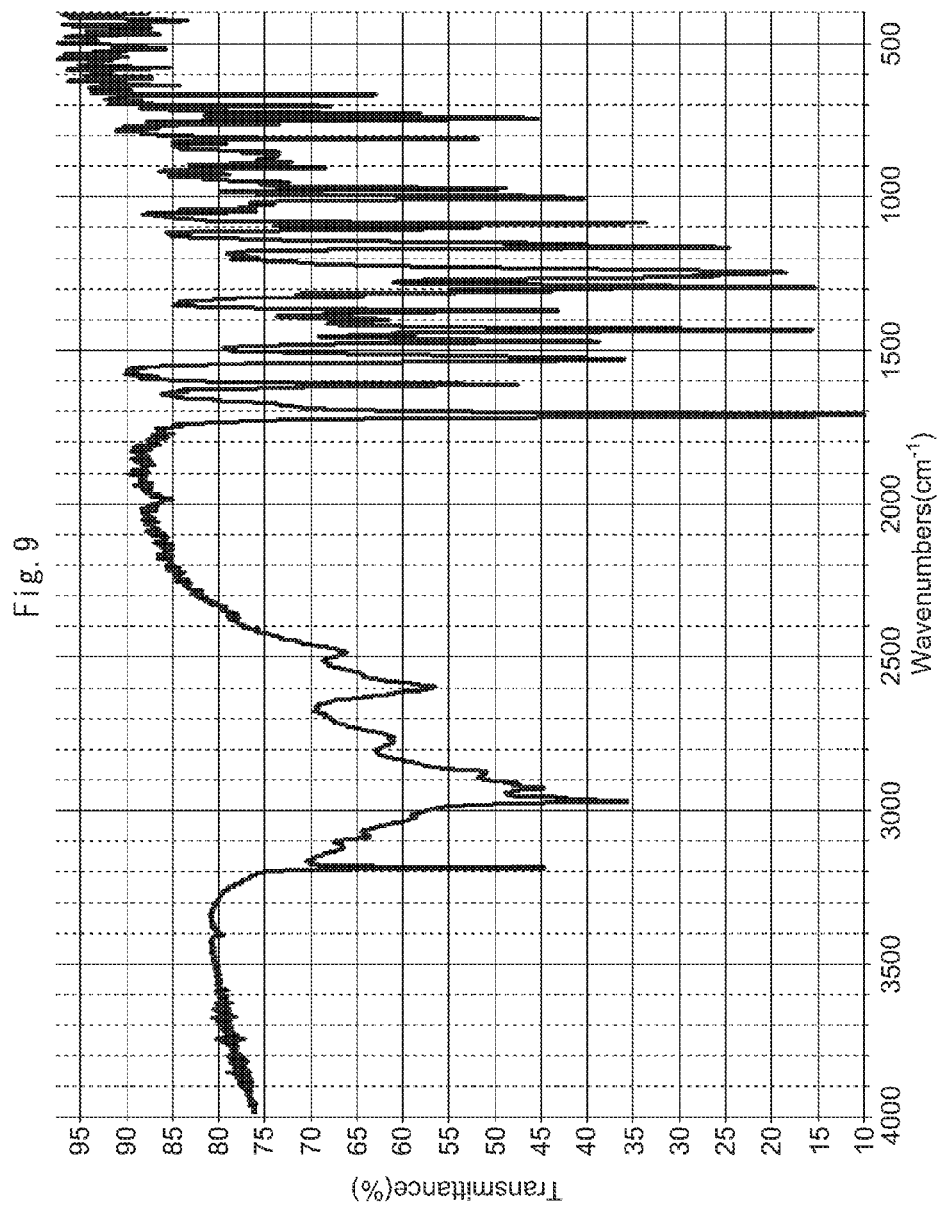
FIG. 9 is an infrared absorption spectrum (KBr method) of crystal form B of the compound (I).

A suspension prepared by suspending 3.0 g of the crystal A of the compound (I) in 21.0 mL of ethyl acetate was subjected to heating under reflux for 6 hours. The suspension was cooled to 25° C. and stirred at 25° C. for 30 minutes. The resulting crystals were filtered out and washed with 15 mL of ethyl acetate. The crystals were vacuum dried at 45° C. to obtain 2.9 g of crystals of 4-methyl-2-[4-(2-methylpropoxy)-3-(1H-1,2,3,4-tetrazol-1-yl)phenyl-1,3-thiazole-5-carboxylic acid. The XRD of the resultant crystals is shown in FIG. 2. Peaks were observed at diffraction angles of 2θ=10.1°, 12.6°, 13.1°, 14.0°, 18.6°, 24.2°, 25.2°, 25.7°, 27.2° and 30.5°. The solid-state $^{13}$C NMR spectrum of the resultant crystals is shown in FIG. 6. Peaks were observed at chemical shifts=115.4 ppm, 118.0 ppm, 119.8 ppm, 123.2 ppm, 126.4 ppm, 129.1 ppm, 142.7 ppm, 151.2 ppm, 160.9 ppm and 166.6 ppm. The infrared absorption spectrum (KBr method) of the resultant crystals is shown in FIG. 9. Peaks were observed at wave numbers=744 cm$^{-1}$, 810 cm$^{-1}$, 972 cm$^{-1}$, 997 cm$^{-1}$, 1005 cm$^{-1}$, 1611 cm$^{-1}$ and 1710 cm$^{-1}$. In addition, the exothermic peak in thermogravimetry/differential thermal analysis (TG/DTA) was observed at 225° C.

Reference Example 2

Production of 4-methyl-2-[4-(2-methylpropoxy)-3-(1H-1,2,3,4-tetrazol-1-yl)phenyl]-1,3-thiazole-5-carboxylic Acid: Compound (I)

A reaction mixture solution prepared by dissolving 4.00 g of ethyl 4-methyl-2-[4-(2-methylpropoxy)-3-(1H-1,2,3,4-tetrazol-1-yl)phenyl]-1,3-thiazole-5-carboxylate in 60 mL of a mixed solution of tetrahydrofuran/methanol=1/1 and by adding 10.3 ml of 2 M sodium hydroxide aqueous solution to the mixture was stirred at room temperature for 3 hours. After adding 10.3 mL of 2 M hydrochloric acid to the reaction mixture solution under stirring, 60 mL of water was added and the resultant mixture was purified using a conventional method to obtain 3.50 g of 4-methyl-2-[4-(2-methylpropoxy)-3-(1H-1,2,3,4-tetrazol-1-yl)phenyl]-1,3-thiazole-5-carboxylic acid.

$^1$H-NMR (400 MHz, DMSO d6) δ: 0.85 (6H, d, J=6.8 Hz), 1.93-2.00 (1H, m), 2.66 (3H, s), 3.96 (2H, d, J=6.0 Hz), 7.48 (1H, d, J=8.8 Hz), 8.18 (1H, dd, J=2.4, 8.8 Hz), 8.27 (1H, d, J=2.4 Hz), 9.79 (1H, s), 13.41 (1H, s)

Example 3

Production of Crystal Form C of 4-methyl-2-[4-(2-methylpropoxy)-3-(1H-1,2,3,4-tetrazol-1-yl)phenyl]-1,3-thiazole-5-carboxylic Acid: Compound (I)

Figure 3:
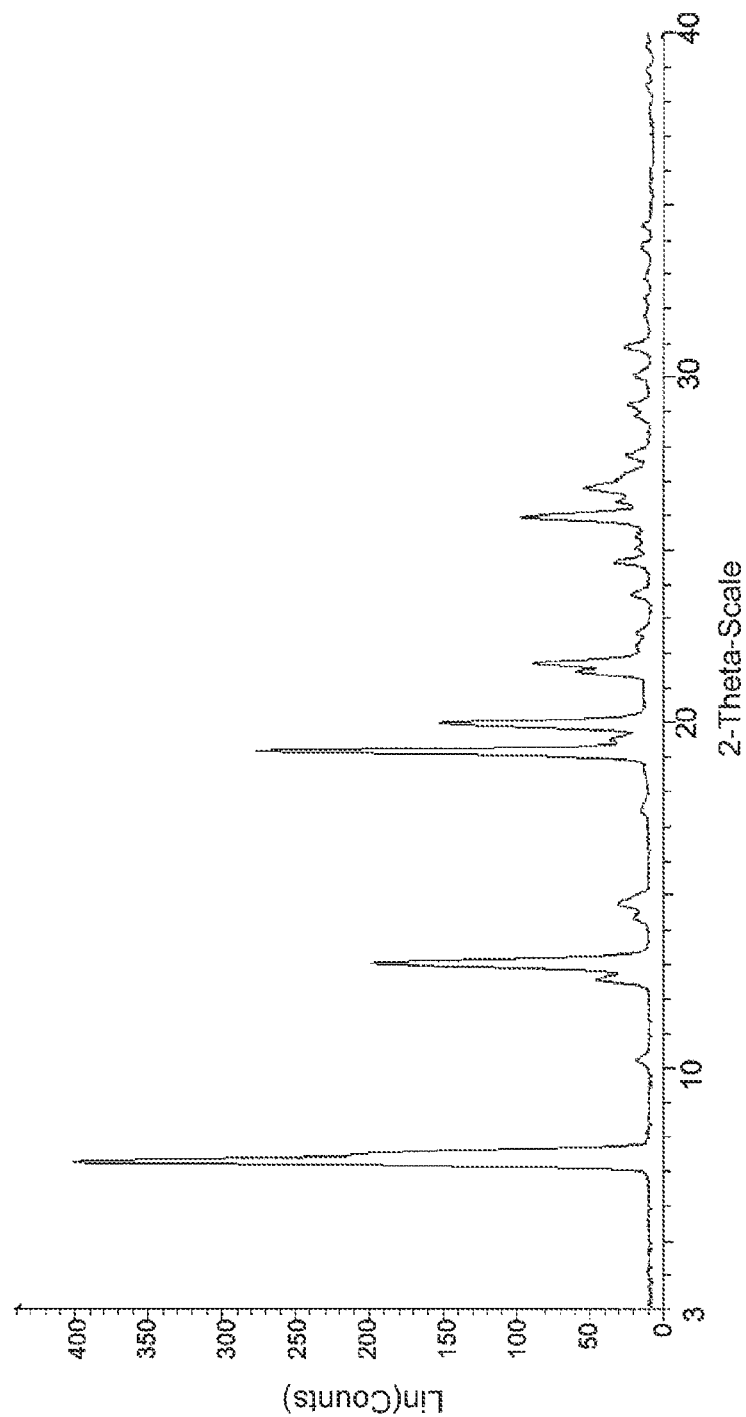
FIG. 3 is a powder X-ray diffraction spectrum of crystal form C of the compound (I).
Figure 7:
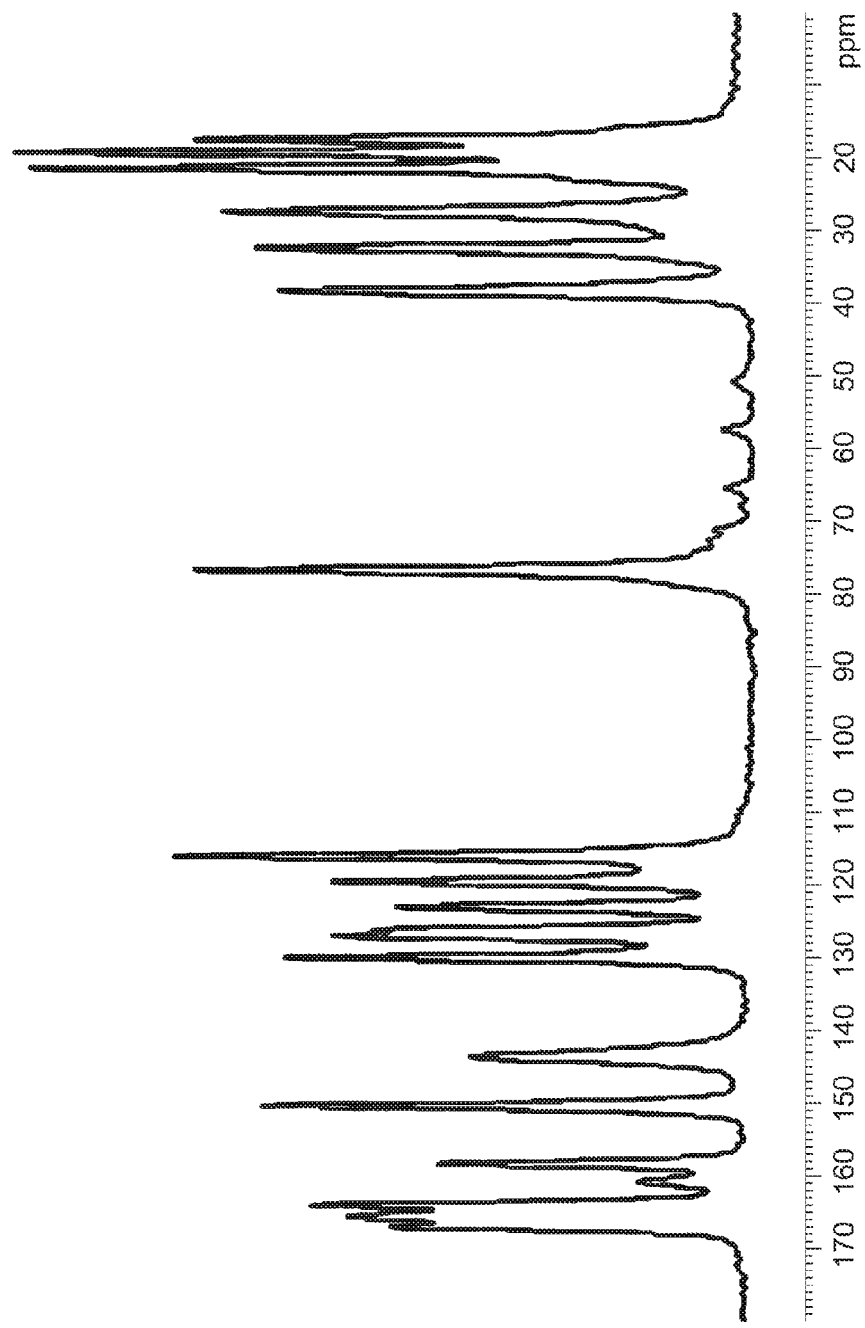
FIG. 7 is a solid-state $^{13}$C NMR spectrum of crystal form C of the compound (I).
Figure 10:
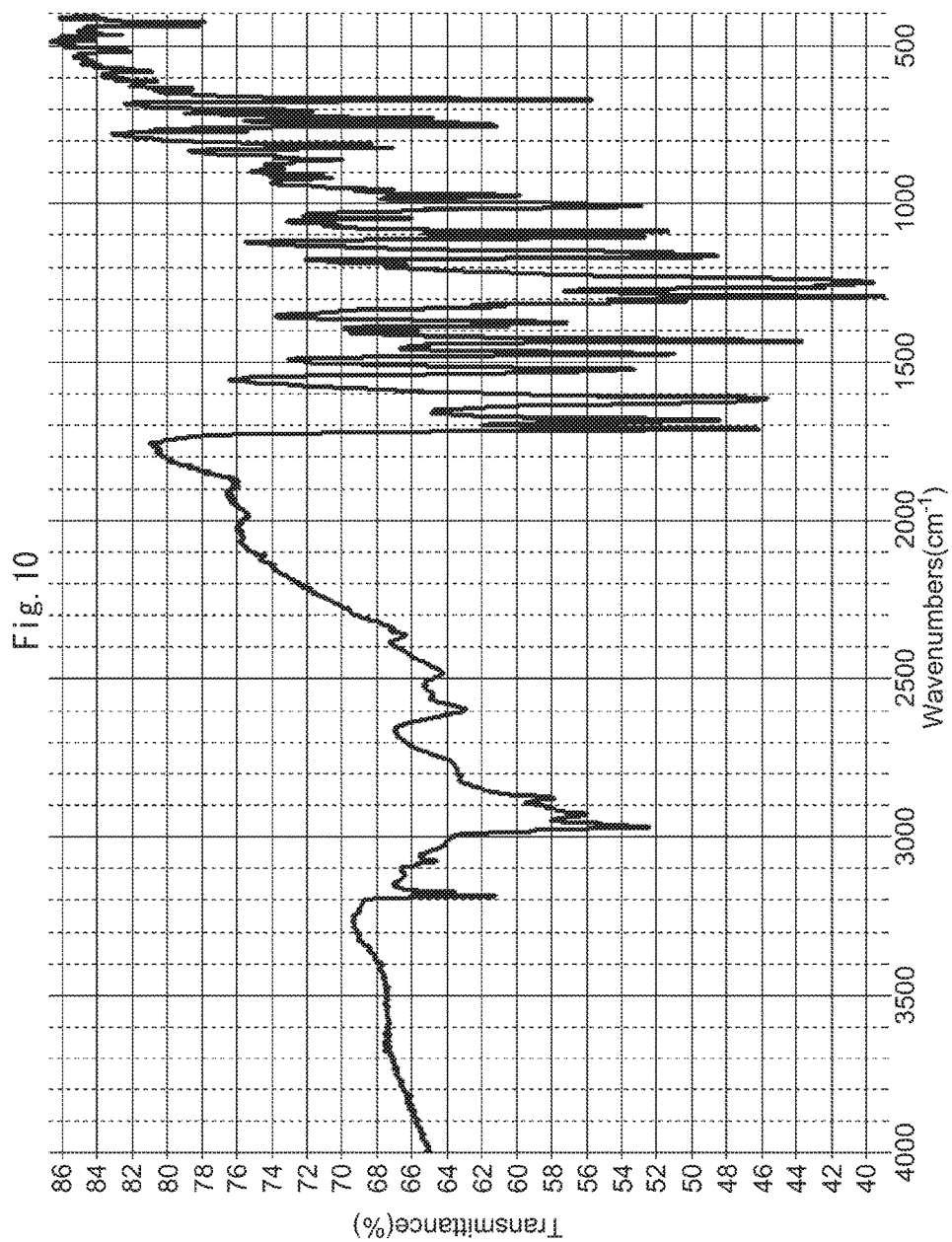
FIG. 10 is an infrared absorption spectrum (KBr method) of crystal form C of the compound (I).

A mixture prepared by adding 90 mL of N,N-dimethylformamide to 8.5 g of 4-methyl-2-[4-(2-methylpropoxy)-3-(1H-1,2,3,4-tetrazole-1-yl)phenyl-1,3-thiazol-5-carboxylic acid was dissolved by heating and stirring at 80° C. After cooling the solution down to room temperature, it was stirred for 2 hours at room temperature and then filtered. The filtered product was washed with 90 mL of ethanol. The mother liquid was allowed to stand at room temperature for 7 days and the resulting crystals were washed with 30 mL of ethanol. The crystals were vacuum dried at 40° C. to obtain 1.0 g of crystals of the compound (I). The XRD of the resultant crystals is shown in FIG. 3. Peaks were observed at diffraction angles of 2θ=7.2°, 12.5°, 13.0°, 14.7°, 19.2°, 20.0°, 21.4°, 21.7°, 24.7° and 26.0°. The solid-state $^{13}$C NMR spectrum of the resultant crystals is shown in FIG. 7. Peaks were observed at chemical shifts=116.1 ppm, 119.6 ppm, 123.1 ppm, 126.1 ppm, 127.1 ppm, 130.0 ppm, 143.6 ppm, 150.3 ppm, 158.3 ppm, 160.7 ppm, 163.9 ppm, 165.5 ppm and 167.0 ppm. The infrared absorption spectrum (KBr method) of the resultant crystals is shown in FIG. 10. Peaks were observed at wave numbers=745 cm$^{-1}$, 751 cm$^{-1}$, 809 cm$^{-1}$, 820 cm$^{-1}$, 971 cm$^{-1}$, 1006 cm$^{-1}$, 1613 cm$^{-1}$, 1682 cm$^{-1}$ and 1710 cm$^{-1}$. In addition, the endothermic peak was observed at 88° C. and the exothermic peak at 225° C. in thermogravimetry/differential thermal analysis (TG/DTA).

Example 4

Production of Crystal Form A of Sodium 4-methyl-2-[4-(2-methylpropoxy)-3-(1H-1,2,3,4-tetrazol-1-yl)phenyl]-1,3-thiazole-5-carboxylate: Compound (II)

Figure 4:
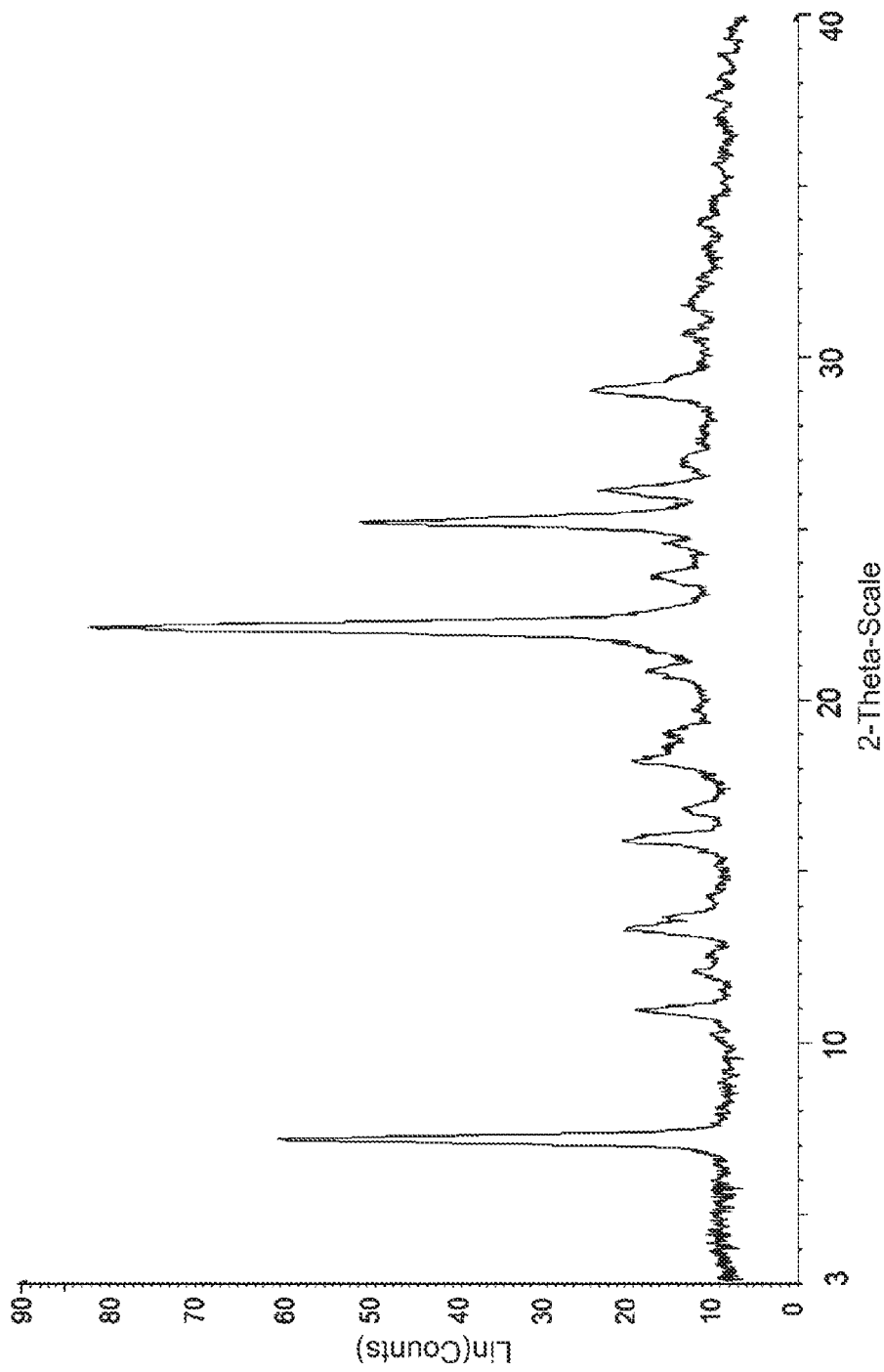
FIG. 4 is a powder X-ray diffraction spectrum of crystal form A of the compound (II).

To a solution prepared by dissolving 400 mg of sodium hydroxide in 36 mL of ethanol, 3.59 g of the compound (I) was added and the resultant mixture was stirred in the range between 20° C. and 30° C. for one hour. Thereafter, the crystals were filtered out. The resulting crystals were washed with 10 mL of ethanol. The crystals were vacuum dried at 50° C. to give 3.53 g the compound (II). The XRD of the resultant crystals is shown in FIG. 4. Peaks were observed at diffraction angles of 2θ=7.2°, 10.9°, 13.3°, 15.9°, 18.2°, 20.8°, 22.1°, 25.2°, 26.1° and 29.1°. In addition, the exothermic peak in thermogravimetry/differential thermal analysis (TG/DTA) was observed at 281° C.

$^1$H-NMR (400 Mz, DMSO-d6) δ:0.85 (6H, d, J=6.8 Hz), 1.92-1.99 (1H, m), 2.59 (3H, s), 3.92 (2H, d, J=6.4 Hz), 7.41 (1H, d, J=8.8 Hz), 8.02 (1H, dd, J=1.6, 8.8 Hz), 8.12 (1H, d, J=2.0 Hz), 9.78 (1H, s)

Example 5

Hypouricemic Effect (Normal Rats)

The hypouricemic effect was confirmed for the compound (II). A test compound suspended in a 0.5% methylcellulose solution was administered to 8 to 9 week-old Sprague-Dawley male rats (Japan Charles River Co.) by oral gavage administration using a feeding needle. After the blood was collected from the tail vein at 2 hours after administration, the plasma was separated. The level of uric acid in the blood sample was measured by uricase method using an absorption spectrometer as well as a uric acid determination kit (L type Wako UA F: Wako Pure Chemical Industries, Ltd.). The percentage of hypouricemic effect was determined by the following expression:

Percentage of hypouricemic effect (%)=(Level of uric acid of the control animal−Level of uric acid of the test compound-administered animal)×100/Level of uric acid of the control animal.

The crystal A of the compound (II) showed a hypouricemic effect of 50% or more at the doses of 10 mg/kg and 1 mg/kg From the above results, it was shown that the compound (II) has a potent hypouricemic effect.

Example 6

Prolonged Hypouricemic Effect (Normal Rats)

The crystal form A of the compound (II) was administered to Sprague-Dawley male rats in the similar manner as Example 5.

After the blood was collected from the tail vein 24 hours after administration, the plasma was separated. The level of uric acid in the blood was measured by an uricase method using an absorption spectrometer and a uric acid determination kit (L type Wako UA F: Wako Pure Chemical Industries, Ltd.). The percentage of hypouricemic effect was determined by the following expression:

Percentage of hypouricemic effect=(Level of uric acid of the control animal−Level of uric acid of the test compound-administered animal)×100/Level of uric acid of the control animal.

The crystal form A of the compound (II) showed a hypouricemic effect of 50% or more in 24 hours after administration at the dose of 10 mg/kg and 40% or more in 24 hours after administration at the dose of 3 mg/kg From the above results, it was shown that the crystal form A of the compound (II) has a prolonged hypouricemic effect over a long period of time.

Example 7

Solubility into JP2 Solution

The solubility of the compound (II) in JP2 solution (pH 6.8) was confirmed. A solution was prepared by mildly pulverizing the crystals A of the compound (II) in a mortar, and adding approximately 4 mg of the pulverized crystals to 20 of JP2 solution while stirring at room temperature. The absorbance (At) of each solution at 280 nm was successively measured immediately after the addition of the crystals using an ultraviolet-visible absorbance measurement method and the solubility at each measurement time was determined by the following expression using the absorbance (As) of a standard solution at 280 mu determined in advance as an index. The measurement was continued until 120 minutes. Solubility=At/As×Cs (where Cs represents the concentration of a standard solution)

Measurement Conditions

Measurement apparatus: μDISS Profiler manufactured by Pion Inc.

Stirring rate: 700 rpm

UV measurement wavelength: 280 nm

Measurement interval: Start of measurement to 1 minute: 3 seconds 1 to 8 minutes: 20 seconds 8 to 120 minutes: 2 minutes The total amount of the crystal A of the compound (II) was dissolved within 30 seconds after the addition and the solubility of the crystal A of the compound (II) was 187 μg/mL. In addition, the solubility at 120 minutes after the addition was 184 μg/mL, no precipitation was observed and a dissolved state was maintained.

From the above results, it was shown that the compound (II) has an excellent solubility.

Reference Example 3

Measurement of Xanthine Oxidase Inhibitory Activity (1) Preparation of Test Compound After dissolving the compound (I) in DMSO (produced by Sigma Corporation) to make the concentration at 20 mM, the resultant solution was used by adjusting the concentration to a desired value for the purpose during use.

(2) Measurement Method

The evaluation of the xanthine oxidase inhibitory activity of the compound (I) was conducted by the method described in the reference (Method Enzymatic Analysis, 1, 521-522, 1974) with partial modification. This evaluation was carried out by measuring oxidase-type xanthine oxidoreductase activity. Concretely, a xanthine (manufactured by Sigma Co.) solution was prepared at 10 mM using a 20 mM sodium hydroxide solution and then mixed with 100 mM phosphate buffer to adjusted to 30 μM. 75 μL of the solution was added to each well of the 96-well plate. The test compound diluted with DMSO at 100 times of a final concentration was added to each well at 1.5 μL per well. After mixing the plate, absorbance at 290 nm was measured by a microplate reader SPECTRA MAX Plus 384 (manufactured by Molecular Devices, LLC). Subsequently, oxidase-type xanthine oxidoreductase (from buttermilk, manufactured by Calbiochem Novabiochem Corp.) was prepared at 30.6 mU/mL using a 100 mM phosphate buffer solution and added to each well at 73.5 μL per well. Immediately after mixing, the change of absorbance at 290 nm was measured for 5 minutes. The enzyme activity of DMSO solution without test compound was used as 100% control, and the inhibitory rate of the test compounds was calculated. Fifty percent inhibitory concentration of the test compounds on the oxidase-type xanthine oxidoreductase activity was calculated by fitting to the dose-response curve.

The compound (I) showed a xanthine oxidase inhibitory activity of $1.0\ nM \leq IC_{50} < 5.0\ nM$.

Reference Example 4

Hypouricemic Effect (Normal Rats)

The hypouricemic effect was confirmed for the compound (I) using the similar manner as in Example 5. The compound (I) showed a hypouricemic effect of 50% or more in both doses of 10 mg/kg and 1 mg/kg From the above results, it was shown that the compound (I) has a potent hypouricemic effect.

Reference Example 5

Prolonged Hypouricemic Effect (Normal Rats)

Prolonged hypouricemic effect was confirmed for the compound (I) in the similar manner as in Example 6.

The compound (I) showed a hypouricemic effect of 50% or more in 24 hours after administration at the dose of 10 mg/kg and 40% or more in 24 hours after administration at the dose of 3 mg/kg.

From the above results, it was shown that the compound (I) has a prolonged hypouricemic effect over a long period of time.

Reference Example 6

Hypouricemic Effect (Hyperuricemic Beagle Dogs)

The hypouricemic effect was confirmed for the compounds (I) in oxonic acid-induced hyperuricmic beagle dog. A test compound suspended in a 0.5% methylcellulose solution was administered to beagle dog (Kitayama labes) by oral gavage administration. Potassium oxonate (50 mg/kg) was subcutaneously administrated before and 4 hours after compound administration. After the blood was collected from the cephalic vein at 8 hours after administration, the plasma was separated. The level of uric acid in the plasma sample was measured by LC-MS/MS method and the percentage of hypouricemic effect was determined by the following expression:

Percentage of hypouricemic effect (%)=(Level of uric acid of the control animal−Level of uric acid of the test compound-administered animal)×100/Level of uric acid of the control animal.

The compound (I) showed a hypouricemic effect at the dose of 10 mg/kg at 8 hours after administration.

From the above results, it was shown that the compound (I) has a potent hypouricemic effect in beagle dog.

Reference Example 7

Prolonged inhibitory effect of xanthine oxidase in tissue and plasma.

For "xanthine oxidase" in the present invention, as far as this example, oxidative reaction catalyzing activities which are brought by oxidase-type xanthine oxidoreductase solely and by both oxidase-type and dehydrogenase-type xanthine oxidoreductase are distinguished. The former is "XO activity" and the latter is "XOR activity". In "tissue XO activity", "plasma XO activity", "tissue XOR activity inhibition", "tissue XOR activity inhibition" and the like, "XO activity" and "XOR activity" have the same meanings as defined above. The tissue includes liver, kidney, adipose tissue, intestine and vessel. In addition, percentage of XO activity inhibition and that of XO activity inhibition in same sample are thought to be similar, according to the results below.

The inhibitory effect of tissue XO activity tissue XOR activity and plasma XO activity was confirmed for the compounds (I). A test compound suspended in a 0.5% methylcellulose solution was administered to 7 to 9 week-old Sprague-Dawley male rats (Japan Charles River Co.) by oral gavage administration using a feeding needle. The blood was collected from the abdominal vein and tissue was collected at 24 or 27 hours after administration. Plasma sample was prepared by centrifugation.

Tissue XO activity, tissue XOR activity and plasma XO activity were measured by the pterin-based assay which utilizes the reaction that pterin is oxidized by each type of xanthine oxidoreductase to produce fluorescent isoxanthopterin. In brief, frozen tissues were homogenized with potassium phosphate buffer, pH 7.4, containing 1 mM ethylenediaminetetraacetic acid (EDTA) and protease inhibitors to prepare tissue concentration as follow (liver: 25 mg/mL, kidney: 25 mg/mL, intestine: 5 mg/mL, adipose tissue: 5 mg/mL, vessel: 30 mg/mL). Then the homogenates were centrifuged 12,000 rpm for 15 min at 4° C. When measured XO activity, the supernatant of tissue and plasma were respectively co-incubated with 50 μM pterin solution at 37° C. When measured XOR activity, the supernatant of tissue homogenate was co-incubated with 50 μM pterin and 50 μM methylene blue solution at 37° C. As a control, oxidase-type xanthine oxidoreductase (from buttermilk, manufactured by Calbiochem Novabiochem Corp.) was also incubated with pterin solution in the same manner. XO activity and XOR activity of the samples were determined from fluorescence intensity which normalized by the intensity value of control and protein concentration.

The percentage of XO activity inhibition and XOR activity inhibition were determined by the following expression:

Percentage of XO or XOR activity inhibition (%)= (XO or XOR activity of the control animal−XO or XOR activity of the test compound-administered animal)×100/XO or XOR activity of the control animal.

Tissue and plasma activities and plasma XO activity at 27 hours after administration are shown in the following table.

TABLE 1

XO inhibitory activity of tissue and plasma (at the dissection about 27 hours after administration) % of inhibition (vs. vehicle)

| | Dosage (mg/Kg) | |
|---|---|---|
| | 1 | 10 |
| Liver | ≥80% | ≥80% |
| Kidney | ≥60% | ≥70% |
| Plasma | ≥25% | ≥40% |

The compound (I) inhibited 80% or more XO activity at 27 hours after drug administration compared to the control animal at the dose of 10 mg/kg in liver.

The compound (I) inhibited 70% or more XO activity at 27 hours after drug administration compared to the control animal at the dose of 10 mg/kg in kidney.

The compound (I) inhibited 40% or more XO activity at 27 hours after drug administration compared to the control animal at the dose of 10 mg/kg in plasma.

The compound (I) inhibited 80% or more XO activity at 27 hours after drug administration compared to the control animal at the dose of 1 mg/kg in liver.

The compound (I) inhibited 60% or more XO activity at 27 hours after drug administration compared to the control animal at the dose of 1 mg/kg in kidney.

The compound (I) inhibited 25% or more XO activity at 27 hours after drug administration compared to the control animal at the dose of 1 mg/kg in plasma.

In addition, the tissue XO and XOR inhibitory activity at 24 hours after administration is shown in the following table.

TABLE 2

XO and XOR inhibitory activity of tissue (at dissection about 24 hours after administration) % of inhibition (vs. vehicle)

| | | Dose (mg/kg) | |
|---|---|---|---|
| | | 1 | 10 |
| Liver | XOR | ≥80% | ≥80% |
| Liver | XO | ≥80% | ≥80% |
| Kidney | XOR | ≥60% | ≥70% |
| Kidney | XO | ≥60% | ≥70% |
| Intestines | XOR | ≥60% | ≥80% |
| Fat | XOR | ≥30% | ≥60% |
| Vessel | XOR | ≥25% | ≥40% |

The compound (I) inhibited 80% or more XOR activity and XO activity at 24 hours after drug administration compared to the control animal at the dose of 10 mg/kg in liver.

The compound (I) inhibited 70% or more XOR activity and XO activity at 24 hours after drug administration compared to the control animal at the dose of 10 mg/kg in kidney.

The compound (I) inhibited 80% or more XOR activity at 24 hours after drug administration compared to the control animal at the dose of 10 mg/kg in intestines.

The compound (I) inhibited 60% or more XOR activity at 24 hours after drug administration compared to the control animal at the dose of 10 mg/kg in fat tissues.

The compound (I) inhibited 40% or more XOR activity at 24 hours after drug administration compared to the control animal at the dose of 10 mg/kg in vessel.

The compound (I) inhibited 80% or more XOR activity and XO activity at 24 hours after drug administration compared to the control animal at the dose of 1 mg/kg in liver.

The compound (I) inhibited 60% or more XOR activity and XO activity at 24 hours after drug administration compared to the control animal at the dose of 1 mg/kg in kidney.

The compound (I) inhibited 60% or more XOR activity at 24 hours after drug administration compared to the control animal at the dose of 1 mg/kg in intestines.

The compound (I) inhibited 30% or more XOR activity at 24 hours after drug administration compared to the control animal at the dose of 1 mg/kg in fat tissues.

The compound (I) inhibited 25% or more XOR activity at 24 hours after drug administration compared to the control animal at the dose of 1 mg/kg in vessel.

From the above results, it was shown that the compounds of the present invention have a prolonged inhibitory effect of XO activity or XOR activity.

INDUSTRIAL APPLICABILITY

The crystal of the compound (I), and the salt and the crystal of the compound (II) of the present invention are used as a pharmaceutical agent. Furthermore, these compounds can be used as an active pharmaceutical ingredient for producing a pharmaceutical agent.

The invention claimed is:

1. A crystal form A of 4-methyl-2-[4-(2-methylpropoxy)-3-(1H-1,2,3,4-tetrazol-1-yl)phenyl]-1,3-thiazole-5-carboxylic acid.

2. The crystal according to claim 1, wherein the crystal has characteristic peaks at diffraction angles of 2θ (±0.5°)=8.6°, 10.2°, 13.3°, 14.4°, 18.5°, 19.9°, 21.8°, 25.1°, 25.6°, 26.6°, 27.1° and 29.5° in its powder X-ray diffraction spectrum, wherein X-ray diffraction spectrum is obtained with Cu Kα as radiation source.

3. The crystal according to claim 1, wherein its powder X-ray diffraction spectrum has a pattern shown in FIG. 1, wherein X-ray diffraction spectrum is obtained with Cu Kα as radiation source.

4. The crystal according to claim 1, wherein the crystal has characteristic peaks at chemical shifts (±0.5 ppm) of 116.3 ppm, 117.6 ppm, 120.0 ppm, 123.6 ppm, 125.9 ppm, 127.4 ppm, 143.7 ppm, 151.8 ppm, 161.1 ppm, 162.3 ppm and 165.5 ppm in its solid-state $^{13}$C NMR spectrum.

5. The crystal according to claim 1, wherein its solid-state $^{13}$C NMR spectrum has a pattern shown in FIG. 5.

6. The crystal according to claim 1, wherein the crystal has characteristic peaks at wave numbers (±5 cm$^{-1}$) of 745 cm$^{-1}$, 822 cm$^{-1}$, 889 cm$^{-1}$, 975 cm$^{-1}$, 997 cm$^{-1}$, 1611 cm$^{-1}$ and 1705 cm$^{-1}$ infrared absorption spectrum (KBr method).

7. The crystal according to claim 1, wherein its infrared absorption spectrum (KBr method) has a pattern shown in FIG. 8.

8. The crystal according to claim 1, wherein its exothermic peak in thermogravimetry/differential thermal analysis is at 222° C.±2° C.

9. A crystal form B of 4-methyl-2-[4-(2-methylpropoxy)-3-(1H-1,2,3,4-tetrazol-1-yl)phenyl]-1,3-thiazole-5-carboxylic acid.

10. The crystal according to claim 9, wherein the crystal has characteristic peaks at diffraction angles of 2θ (±0.5°)=10.1°, 12.6°, 13.1°, 14.0°, 18.6°, 24.2°, 25.2°, 25.7°, 27.2° and 30.5° in its powder X-ray diffraction spectrum, wherein X-ray diffraction spectrum is obtained with Cu Kα as radiation source.

11. The crystal according to claim 9, wherein its powder X-ray diffraction spectrum has a pattern shown in FIG. 2, wherein X-ray diffraction spectrum is obtained with Cu Kα as radiation source.

12. The crystal according to claim 9, wherein the crystal has characteristic peaks at chemical shifts (±0.5 ppm) of 115.4 ppm, 118.0 ppm, 119.8 ppm, 123.2 ppm, 126.4 ppm, 129.1 ppm, 142.7 ppm, 151.2 ppm, 160.9 ppm and 166.6 ppm in its solid-state $^{13}$C NMR spectrum.

13. The crystal according to claim 9, wherein its solid-state $^{13}$C NMR spectrum has a pattern shown in FIG. 6.

14. The crystal according to claim 9, wherein the crystal has characteristic peaks at wave numbers (±5 cm$^{-1}$) of 744 cm$^{-1}$, 810 cm$^{-1}$, 972 cm$^{-1}$, 997 cm$^{-1}$, 1005 cm$^{-1}$, 1611 cm$^{-1}$ and 1710 cm$^{-1}$ in its infrared absorption spectrum (KBr method).

15. The crystal according to claim 9, wherein its infrared absorption spectrum (KBr method) has a pattern shown in FIG. 9.

16. The crystal according to claim 9, wherein its exothermic peak in thermogravimetry/differential thermal analysis is at 225° C.±2° C. and it is an anhydrous crystal.

17. A crystal form C of 4-methyl-2-[4-(2-methylpropoxy)-3-(1H-1,2,3,4-tetrazol-1-yl)phenyl]-1,3-thiazole-5-carboxylic acid.

18. The crystal according to claim 17, wherein the crystal has characteristic peaks at diffraction angles of 2θ (±0.5°)=7.2°, 12.5°, 13.0°, 14.7°, 19.2°, 20.0°, 21.4°, 21.7°, 24.7° and 26.0 in its powder X-ray diffraction spectrum, wherein X-ray diffraction spectrum is obtained with Cu Kα as radiation source.

19. The crystal according to claim 17, wherein its powder X-ray diffraction spectrum has a pattern shown in FIG. 3, wherein X-ray diffraction spectrum is obtained with Cu Kα as radiation source.

20. The crystal according to claim 17, wherein the crystal has characteristic peaks at chemical shifts (±0.5 ppm) of 116.1 ppm, 119.6 ppm, 123.1 ppm, 126.1 ppm, 127.1 ppm, 130.0 ppm, 143.6 ppm, 150.3 ppm, 158.3 ppm, 160.7 ppm, 163.9 ppm, 165.5 ppm and 167.0 ppm in its solid-state $^{13}$C NMR spectrum.

21. The crystal according to claim 17, wherein its solid-state $^{13}$C NMR spectrum has a pattern shown in FIG. 7.

22. The crystal according to claim 17, wherein the crystal has characteristic peaks at wave numbers (±5 cm$^{-1}$) of 745 cm$^{-1}$, 751 cm$^{-1}$, 809 cm$^{-1}$, 820 cm$^{-1}$, 971 cm$^{-1}$, 1006 cm$^{-1}$, 1613 cm$^{-1}$, 1682 cm$^{-1}$ and 1710 cm$^{-1}$ in its infrared absorption spectrum (KBr method).

23. The crystal according to claim 17, wherein its infrared absorption spectrum (KBr method) has a pattern shown in FIG. 10.

24. The crystal according to claim 17, wherein its endothermic peak is at 88° C.±2° C. and exothermic peak is at 225° C.±2° C. in thermogravimetry/differential thermal analysis.

25. A pharmaceutical composition comprising the crystal form A according to claim 1 and a pharmaceutically acceptable carrier.

26. A xanthine oxidase inhibitor comprising the crystal form A according to claim 1 as an active ingredient.

27. A method for treating diseases selected from the group consisting of gout, hyperuricemia, tumor lysis syndrome, urinary calculi, hypertension, dyslipidemia, diabetes, arteriosclerosis, heart failure, diabetic nephropathy, chronic obstructive pulmonary diseases, and inflammatory bowel diseases;
or preventing diseases selected from the group consisting of gout, arteriosclerosis, and diabetic nephropathy; comprising administering an effective amount of the crystal form A according to claim 1 as an active ingredient.

28. A method for producing the crystal form A of 4-methyl-2-[4-(2-methylpropoxy)-3-(1H-1,2,3,4-tetrazol-1-yl)phenyl]-1,3-thiazole-5-carboxylic acid, comprising the steps of:
suspending an alkyl ester of 4-methyl-2-[4-(2-methylpropoxy)-3-(1H-1,2,3,4-tetrazol-1-yl)phenyl]-1,3-thiazole-5-carboxylic acid in a solvent and performing hydrolysis by adding an aqueous solution of a base thereto; and
neutralizing the reaction product.

29. The method for production according to claim 28 further comprising the step of adding water to the neutralized product and stirring it.

30. A method for producing the crystal form B of 4-methyl-2-[4-(2-methylpropoxy)-3-(1H-1,2,3,4-tetrazol-1-yl)phenyl]-1,3-thiazole-5-carboxylic acid, comprising the step of suspending the crystal form A of 4-methyl-2-[4-(2-methylpropoxy)-3-(1H-1,2,3,4-tetrazol-1-yl)phenyl]-1,3-thiazole-5-carboxylic acid in a solvent.

31. The method of production according to claim 30, further comprising the step of heating the suspension.

32. The method for producing the crystal according to claim 30, wherein the solvent is selected from the group consisting of ethers, ketones, esters, alcohols, water, and a mixture solvent thereof.

33. A method for producing the crystal form C of 4-methyl-2-[4-(2-methylpropoxy)-3-(1H-1,2,3,4-tetrazol-1-yl)phenyl]-1,3-thiazole-5-carboxylic acid, comprising crystallization from an N,N-dimethylformamide solution thereof.

34. A pharmaceutical composition comprising the crystal form B according to claim 9 and a pharmaceutically acceptable carrier.

35. A xanthine oxidase inhibitor comprising the crystal form B according to claim 9 as an active ingredient.

36. A method for treating diseases selected from the group consisting of gout, hyperuricemia, tumor lysis syndrome, urinary calculi, hypertension, dyslipidemia, diabetes, arteriosclerosis, heart failure, diabetic nephropathy, chronic obstructive pulmonary diseases, and inflammatory bowel diseases;
or preventing diseases selected from the group consisting of gout, arteriosclerosis, and diabetic nephropathy; comprising administering an effective amount of the crystal form B according to claim 9 as an active ingredient.

37. A pharmaceutical composition comprising the crystal form C according to claim 17 and a pharmaceutically acceptable carrier.

38. A xanthine oxidase inhibitor comprising the crystal form C according to claim 17 as an active ingredient.

39. A method for treating diseases selected from the group consisting of gout, hyperuricemia, tumor lysis syndrome, urinary calculi, hypertension, dyslipidemia, diabetes, arteriosclerosis, heart failure, diabetic nephropathy, chronic obstructive pulmonary diseases, and inflammatory bowel diseases;
or preventing diseases selected from the group consisting of gout, arteriosclerosis, and diabetic nephropathy; comprising administering an effective amount of the crystal form C according to claim 17 as an active ingredient.

* * * * *